United States Patent
Laurent et al.

(10) Patent No.: US 9,266,902 B2
(45) Date of Patent: Feb. 23, 2016

(54) LABELLING REAGENTS HAVING A PYRIDINE NUCLEUS BEARING A DIAZOMETHYL FUNCTION, PROCESS FOR SYNTHESIS OF SUCH REAGENTS AND PROCESSES FOR DETECTION OF BIOLOGICAL MOLECULES

(75) Inventors: Alain Laurent, Grenoble (FR); Ali Laayoun, Colombe (FR); Mitsuhara Kotera, Strasbourg (FR)

(73) Assignees: BIOMERIEUX, Marcy L'etoile (FR); UNIVERSITE DE STRASBOURG, Strasbourg (FR); CNRS, Paris (FR)

( * ) Notice: Subject to any disclaimer, the term of this patent is extended or adjusted under 35 U.S.C. 154(b) by 810 days.

(21) Appl. No.: 13/001,712

(22) PCT Filed: Jul. 28, 2009

(86) PCT No.: PCT/FR2009/051511
§ 371 (c)(1),
(2), (4) Date: Dec. 28, 2010

(87) PCT Pub. No.: WO2010/012949
PCT Pub. Date: Feb. 4, 2010

(65) Prior Publication Data
US 2011/0111514 A1  May 12, 2011

(30) Foreign Application Priority Data
Jul. 29, 2008 (FR) ........................ 08 55190

(51) Int. Cl.
C07D 333/24 (2006.01)
C07D 233/32 (2006.01)
(Continued)

(52) U.S. Cl.
CPC ............ *C07D 495/04* (2013.01); *C07D 213/24* (2013.01); *C07D 233/32* (2013.01); *C07D 333/24* (2013.01); *Y10T 436/143333* (2015.01)

(58) Field of Classification Search
CPC .. C07D 333/24; C07D 233/32; C07D 213/24; C07D 495/04
USPC ........................... 514/338; 546/274.4; 436/94
See application file for complete search history.

(56) References Cited

U.S. PATENT DOCUMENTS

| 4,507,466 A | 3/1985 | Tomalia et al. |
| 4,568,737 A | 2/1986 | Tomalia et al. |

(Continued)

FOREIGN PATENT DOCUMENTS

| DE | 39 10 151 A1 | 10/1990 |
| EP | 0 063 879 A2 | 11/1982 |

(Continued)

OTHER PUBLICATIONS

Ma; Tetrahedron Letters 46 (2005) 3927-3929.*

(Continued)

*Primary Examiner* — Janet L Andres
*Assistant Examiner* — Daniel Carcanague
(74) *Attorney, Agent, or Firm* — Oliff PLC

(57) ABSTRACT

A process for synthesis of a labelling reagent, a process for the labelling of a biological molecule, a labelled biological molecule obtained by the process, a process for labelling and fragmentation of a single or double strand nucleic acid, a labelled nucleic acid capable of being obtained by the process, a kit for detection of a target nucleic acid containing a labelled nucleic acid, a solid support onto which is attached a reagent and a process for capture of nucleic acids.

23 Claims, 6 Drawing Sheets

(51) Int. Cl.
*C07D 213/24* (2006.01)
*C07D 495/04* (2006.01)

(56) References Cited

U.S. PATENT DOCUMENTS

| | | | |
|---|---|---|---|
| 4,672,040 A | 6/1987 | Josephson | |
| 4,683,195 A | 7/1987 | Mullis et al. | |
| 4,683,202 A | 7/1987 | Mullis | |
| 4,775,745 A | 10/1988 | Ford et al. | |
| 4,800,159 A | 1/1989 | Mullis et al. | |
| 5,234,809 A | 8/1993 | Boom et al. | |
| 5,328,824 A | 7/1994 | Ward et al. | |
| 5,399,491 A | 3/1995 | Kacian et al. | |
| 5,449,767 A | 9/1995 | Ward et al. | |
| 5,489,653 A | 2/1996 | Charles et al. | |
| 5,695,936 A | 12/1997 | Mandrand et al. | |
| 5,750,338 A | 5/1998 | Collins et al. | |
| 6,033,853 A | 3/2000 | Delair et al. | |
| 6,083,708 A | 7/2000 | Singh et al. | |
| 6,083,762 A | 7/2000 | Papen et al. | |
| 6,083,763 A | 7/2000 | Balch | |
| 6,110,426 A | 8/2000 | Shalon et al. | |
| 6,133,047 A | 10/2000 | Elaissari et al. | |
| 6,197,768 B1* | 3/2001 | Ohashi et al. | 514/233.2 |
| 6,376,179 B1 | 4/2002 | Laayoun | |
| 6,489,114 B2 | 12/2002 | Laayoun et al. | |
| 6,521,341 B1 | 2/2003 | Elaissari et al. | |
| 6,537,783 B1 | 3/2003 | Guillou-Bonnici et al. | |
| 6,576,448 B2 | 6/2003 | Weissman et al. | |
| 6,632,662 B1 | 10/2003 | Broyer et al. | |
| 6,660,472 B1 | 12/2003 | Santoro et al. | |
| 6,686,195 B1 | 2/2004 | Colin et al. | |
| 6,818,398 B2 | 11/2004 | Bavykin et al. | |
| 6,875,858 B1 | 4/2005 | DeFrancq et al. | |
| 7,060,441 B2 | 6/2006 | Bourget et al. | |
| 7,338,805 B2 | 3/2008 | Bourget et al. | |
| 7,691,635 B2 | 4/2010 | Laayoun et al. | |
| 2002/0081586 A1 | 6/2002 | Laayoun et al. | |
| 2002/0155496 A1 | 10/2002 | Charles et al. | |
| 2004/0005614 A1 | 1/2004 | Kurn et al. | |
| 2004/0091451 A1 | 5/2004 | Charreyre et al. | |
| 2008/0032288 A1* | 2/2008 | Laayoun et al. | 435/6 |
| 2010/0136538 A1 | 6/2010 | Laurent et al. | |

FOREIGN PATENT DOCUMENTS

| | | |
|---|---|---|
| EP | 0 097 373 A2 | 1/1984 |
| EP | 0 201 184 A2 | 12/1986 |
| EP | 0 286 898 A2 | 10/1988 |
| EP | 0 302 175 A2 | 2/1989 |
| EP | 0 329 198 A2 | 8/1989 |
| EP | 0 350 407 B1 | 1/1990 |
| EP | 0 561 722 A1 | 9/1993 |
| EP | 0 567 841 A2 | 11/1993 |
| EP | 0 569 272 B1 | 11/1993 |
| EP | 0 669 991 B1 | 9/1995 |
| EP | 0 827 552 B1 | 3/1998 |
| FR | 2 607 507 A1 | 6/1988 |
| WO | WO 88/04289 A1 | 6/1988 |
| WO | WO 90/01069 A1 | 2/1990 |
| WO | WO 90/06995 A1 | 6/1990 |
| WO | WO 90/08838 A1 | 8/1990 |
| WO | WO 91/02818 A1 | 3/1991 |
| WO | WO 93/16094 A2 | 8/1993 |
| WO | WO 95/08000 A2 | 3/1995 |
| WO | WO 97/35031 A1 | 9/1997 |
| WO | WO 97/45202 A1 | 12/1997 |
| WO | WO 98/05766 A1 | 2/1998 |
| WO | WO 99/15621 A1 | 4/1999 |
| WO | WO 99/35500 A1 | 7/1999 |
| WO | WO 99/53304 A1 | 10/1999 |
| WO | WO 99/65926 A1 | 12/1999 |
| WO | WO 00/05338 A1 | 2/2000 |
| WO | WO 00/07982 A1 | 2/2000 |
| WO | WO 00/40590 A2 | 7/2000 |
| WO | WO 00/60049 A1 | 10/2000 |
| WO | WO 01/44506 A1 | 6/2001 |
| WO | WO 01/92361 A1 | 12/2001 |
| WO | WO 02/090319 A1 | 11/2002 |
| WO | WO 02/090584 A2 | 11/2002 |
| WO | WO 2005/092910 A1 | 10/2005 |
| WO | WO 2009/001017 A2 | 12/2008 |

OTHER PUBLICATIONS

Foulon; Bioconjugate Chem. 1997, 8, 179-186.*
Chen; J. Org. Chem. 1986, 51, 3325-3334.*
Bae; Mol. Cryst. and Liq. Cryst. 1999, 334, 59-68.*
Ewens; Arch. Toxicol. 1999, 73, 159-167.*
Haddour; J. Am. Chem. Soc. 2006, 128, 9693-9698.*
Fathi; J. Org. Chem. 1996, 61, 5600-5609.*
"2 Methods for the Preparation of Alkane, Alkene, and Alkyne Diazo Compounds," pp. 34-48. Diazo Chemistry II: Aliphatic, Inorganic and Organometallic Compounds. By Heinrich Zollinger 1995 VCH.
E. Bayer et al., "The Use of the Avidin-Biotin Complex as a Tool in Molecular Biology," Methods of Biochemical Analysis, vol. 26 (1980), pp. 1-45.
S. Agrawal, "Protocols for Oligonucleotides and Analogs, Synthesis and Properties," Methods in Molecular Biology, vol. 20, pp. 487-496, Humana Press, New Jersey, 1993.
B. Charleux et al., "Radical-initiated Copolymers of Styrene and p-Formylstyrene, 1 Solution Copolymerization and Characterization," Makromol. Chem., vol. 193 (1992), pp. 187-203.
J. Cheng et al., "Microchip-based Devices for Molecular Diagnosis of Genetic Diseases," Molecular Diagnosis, vol. 1, No. 3 (1996), pp. 183-200.
J. Cheng et al., "Preparation and Hybridization Analysis of DNA/RNA from *E. coli* on Microfabricated Bioelectronic Chips," Nature Biotechnology, vol. 16 (1998), pp. 541-546.
X. Creary, "Tosylhydrazone Salt Pyrolyses: Phenyldiazomethanes," Organic Synthesis, Coll., vol. 7 (1990), pp. 438-443.
M. Egholm et al., "Peptide Nucleic Acids (PNA) Oligonucleotide Analogues with an Achiral Peptide Backbone," J. Am. Chem. Soc., vol. 114 (1992), pp. 1895-1897.
F. Ginot, "Oligonucletide Micro-Arrays for Identification of Unknown Mutations: How Far from Reality?," Human Mutation, vol. 10 (1997), pp. 1-10.
T.W. Greene et al., "Protective Groups in Organic Synthesis," 3$^{rd}$ Edition, John Wiley and Sons, Inc., New York (1991), pp. 230-245.
T. L. Holton et al., "Advantageous Syntheses of Diazo Compounds by Oxidation of Hydrazones with Lead Tetraacetate in Basic Environments," J. Org. Chem. (1995), vol. 60, pp. 4725-4729.
S. Hunt, "The Non-Protein Amino Acids," Chemistry and Biochemistry of the Amino Acids, edited by G.C. Barett, Chapman and Hall, London (1985), pp. 55-138.
W. Jencks et al., "Reactivity of Nucleophilic Reagents toward Esters," J. Amer. Chem Soc., vol. 82 (1960), pp. 1778-1786.
A. Laayoun et al., "Aryldiazomethanes for Universal Labeling of Nucleic Acids and Analysis on DNA Chips," Bioconjugate Chem. (2003), vol. 14, pp. 1298-1306.
P. Langer et al., "Enzymatic Synthesis of Biotin-labeled Polynucleotides: Novel Nucleic Acid Affinity Probes," Proc. Natl. Acad. Sci. USA, vol. 78, No. 11 (1981), pp. 6633-6637.
T. Livache et al., "Preparation of a DNA Matrix Via an Electrochemically Directed Copolymerization of Pyrrole and Oligonucleotides Bearing a Pyrrole Group," Nucleic Acids Research (1994), vol. 22, No. 15, 2915-2921.
G. M. Makrigiorgos et al., "Fluorescent Labeling of Abasic Sites: A Novel Methodology to Detect Closely-Spaced Damage Sites in DNA," Int. J. Radiat. Biol. (1998), vol. 74, No. 1, pp. 99-109.
M. O'Donnell et al., "Reporter Groups for the Analysis of Nucleic Acid Structure," Bioorganic Chemistry: Nucleic Acids, Oxford University Press (1996), pp. 216-243.
M. Oivanen et al., "Kinetics and Mechanisms for the Cleavage and Isomerization of the Phosphodiester Bonds of RNA by Bronsted Acids and Bases," Chem. Rev., vol. 98 (1998), pp. 961-990.
T. Okamoto et al., "Microarray Fabrication with Covalent Attachment of DNA Using Bubble Jet Technology," Nature Biotechnology, vol. 18 (2000), pp. 438-441.

(56) References Cited

OTHER PUBLICATIONS

G. Pratviel et al., "DNA and RNA Cleavage by Metal Complexes," Adv. Org. Chem., vol. 45 (1998), pp. 251-312.

G. Pratviel et al., "Carbon-Hydrogen Bonds of DNA Sugar Units as Targets for Chemical Nucleases and Drugs," Angew. Chem. Int. Ed. Engl., vol. 34 (1995), pp. 746-769.

G. Ramsay, "DNA Chips: State-of-the Art," Nature Biotechnology, vol. 16 (1998), pp. 40-44.

J. Randolph et al., "Stability, Specificity and Fluorescence Brightness of Multiply-labeled Fluorescent DNA Probes," Nucleic Acids Research (1997), vol. 25, No. 14, pp. 2923-2929.

M. Shiga et al., "Synthesis of a Novel Biotin Derivative That Bears a Diazo Group as the Reactive Site," Analytical Sciences (1993), vol. 9, pp. 553-556.

M. Shiga et al., "Fluorescence Detection of DNA Using a Novel Peroxidase Substrate, 4-(4-Hydroxyphenylcarbamoyl)butanoic Acid," Analytical Sciences (1995), vol. 11, pp. 591-595.

D. Sigman et al., "Chemical Nucleases," Chem. Rev., vol. 93 (1993), pp. 2295-2316.

W. C. Still et al., "Rapid Chromatographic Technique for Preparative Separations with Moderate Resolution," J. Org. Chem.(1978), vol. 43, No. 14, pp. 2923-2925.

S. Wong, "Chemistry of Protein Conjugation and Cross-Linking," CRC Press (1991) pp. 16-45.

A. Troesch et al., "Mycobacterium Species Identification and Rifampin Resistance Testing with High-Density DNA Probe Arrays," Journal of Clinical Microbiology (Jan. 1990), vol. 37, No. 1, pp. 49-55.

Jul. 25, 2002 International Search Report issued in International Application No. PCT/FR02/01543.

Aug. 9, 2005 International Search Report issued in International Application No. PCT/FR2005/050192.

Jan. 14, 2009 International Search Report issued in International Application No. PCT/FR2008/051026.

Oct. 12, 2009 International Search Report issued in International Application No. PCT/FR2009/051511.

Jul. 30, 2004 Office Action issued in U.S. Appl. No. 10/137,454, now U.S. Pat. No. 7,338,805 B2.

Feb. 23, 2005 Office Action issued in U.S. Appl. No. 10/137,454, now U.S. Pat. No. 7,338,805 B2.

Jul. 11, 2005 Office Action issued in U.S. Appl. No. 10/137,454, now U.S. Pat. No. 7,338,805 B2.

Feb. 6, 2006 Office Action issued in U.S. Appl. No. 10/137,454, now U.S. Pat. No. 7,338,805 B2.

Mar. 29, 2007 Office Action issued in U.S. Appl. No. 10/137,454, now U.S. Pat. No. 7,338,805 B2.

Mar. 18, 2005 Office Action issued in U.S. Appl. No. 10/137,460, now U.S. Pat. No. 7,060,441 B2.

Jan. 7, 2009 Office Action issued in U.S. Appl. No. 10/590,973, now U.S. Pat. No. 7,691,635.

Jul. 22, 2009 Office Action issued in U.S. Appl. No. 10/590,973, now U.S. Pat. No. 7,691,635.

Eistert et al., "The Diazoketone 'azi-α-pyridil'," Institute of Organic Chemistry, vol. 91, pp. 1411-1415, 1958.

Davies et al., "Catalytic Asymmetric Cyclopropanation of Heteroaryldiazoacetates," J. Org. Chem., vol. 66, pp. 6595-6603, 2001.

Ma et al., "An Efficient Synthesis of Aryl α-Keto Esters," Tetrahedron Letter, vol. 46, pp. 3927-3929, 2005.

\* cited by examiner

LABELLING REAGENTS HAVING A PYRIDINE NUCLEUS BEARING A DIAZOMETHYL FUNCTION, PROCESS FOR SYNTHESIS OF SUCH REAGENTS AND PROCESSES FOR DETECTION OF BIOLOGICAL MOLECULES The present invention relates to novel reagents for labelling of biological molecules, a process for synthesis of the said labels and also applications for the labelling of biological molecules in particular in the field of molecular diagnostics using the detection and analysis of nucleic acids.

The state of the art shows that many methods exist for labelling nucleotides, oligonucleotides or natural or amplified nucleic acids.

A first method consists in attaching the label to the base, whether the latter be natural or modified. A second method proposes attaching the label to the sugar, here again whether it be natural or modified. The subject of a third method is the attachment of the label to the phosphate.

Labelling on the base has in particular been used in the approach of labelling nucleic acids by incorporation of directly labelled nucleotides.

Labelling on the sugar is often used in the case of nucleic acid probes prepared by chemical synthesis.

Labelling on the phosphate has also been used for introducing functionalised arms and labels during the chemical synthesis of oligonucleotides.

In fact, those skilled in the art who have to effect the labelling of a nucleotide or a nucleotide analogue or a nucleic acid, are inclined to effect this attachment onto the base or onto the sugar which offer them more convenience and more alternatives. This is moreover what emerges from the study of many documents, such as EP-A-0.329.198, EP-A-0.302.175, EP-A-0.097.373, EP-A-0.063.879, U.S. Pat. No. 5,449,767, U.S. Pat. No. 5,328,824, WO-A-93/16094, DE-A-39 10 151, EP-A-0.567.841 for the base or EP-A-0.286.898 for the sugar.

The attachment of the label onto the phosphate is a more complex technique than the technique consisting in functionalising the base or the sugar and has been much less used in particular because of the low reactivity of the phosphate (see for example Jencks W. P. et al J. Amer. Chem. Soc., 82, 1778-1785, 1960). Similarly in the review by O'Donnel and Mc Laughlin ("Reporter groups for the analysis of nucleic acid structure", p 216-243, in "Bioorganic Chemistry: Nucleic Acids", Ed. Hecht S. M., Oxford University Press, 1996) relating to methods for introduction of probes into oligonucleotide fragments, the efficient alkylation of the internucleotide phosphodiester is considered to be impossible.

The patent application WO-A-99/65926 describes a process for labelling a synthetic or natural ribonucleic acid (RNA) which consists in fragmenting the RNA and labelling at the terminal phosphate. This document describes a certain number of functions that can be used for labelling in combination with fragmentation such as hydroxyl, amine, hydrazine, alkoxyamine, alkyl halide, and benzyl type alkyl halide functions and in particular the derivative 5-(bromomethyl) fluorescein. These functions make it possible to label the nucleic acids, but it is necessary to include a fragmentation stage in order to have efficient labelling since this labelling takes place on the phosphate liberated during the fragmentation. Moreover, it is necessary to add a considerable excess of labelling reagent relative to the RNA in order to obtain efficient labelling which gives rise to background noise problems during the detection, generated by the excess label. Finally, this method does not function efficiently on double strand DNA.

There is therefore a need for novel reagents which are efficient as regards the labelling yield, which are specific in terms of the labelling position and in particular which do not affect the hybridisation properties of the bases involved in the formation of the double helix, via hydrogen bonds, which are usable both for DNA and RNA, and finally which make it possible indiscriminately to label nucleotides, oligonucleotides, natural nucleic acids or those prepared by transcription, by reverse transcription or by enzymatic amplification.

The applicants have already proposed such novel labels which meet the aforesaid conditions and which use the diazomethyl function as the reactive function for the labelling. This is for example the case in the patent applications WO-A-02/090319, WO-A-02/090584 and WO-A-2005/092910, which are hereby incorporated by reference.

Thus the diazomethyl function (of formula —C($N_2$)—) has already been used for the alkylation of phosphate groups, but a certain number of problems arise. On the one hand, reagents incorporating at least one diazo function are generally unstable in themselves, which poses problems for the use of these reagents in a labelling kit, which is a disadvantage if the function of the labelled product is to demonstrate the presence of a target biological molecule in some sample.

Finally, reagents bearing the diazomethyl function, borne by an aromatic nucleus of the phenyl type to ensure its stability, are linked to certain labels, such as biotin. The presence of the aromatic nucleus and the nature of the label make these reagents poorly soluble in water, which leads to the use of organic solvents which are miscible with water for the coupling with biological molecules, which are only soluble in water or in aqueous buffers. But these solvents, if they are used in too high a concentration in the labelling reaction, may cause the precipitation of the biomolecules. Further, for the automation of the labelling protocols in integrated devices, it is essential to lyophilise the labelling reagents in buffers not containing organic solvents. The latter are not compatible with lyophilisation. It is therefore necessary to be able to have available labelling reagents which are sufficiently soluble and stable in aqueous media.

The labelling reagents advocated by the aforesaid documents WO-A-02/090319, WO-A-02/090584 (first generation molecules) and WO-A-2005/092910 (second generation molecules) also resolve these technical problems.

These molecules thus have the following disadvantages:
chemically unstable, as they have to be dry or in solution at 4° C.,
relatively complex synthesis, and
poorly soluble in an aqueous solution.

In spite of these disadvantages, these molecules are particularly interesting and attractive for those skilled in the art. It is in any case possible to improve their physical or chemical characteristics, which was the priority during the development of the third generation molecules, disclosed in the document WO-A-2009/001017, which is hereby incorporated by reference, in which the molecules are both more stable and easier to synthesise.

This start of a solution made it possible to confront the problem of the stability of the first and second generation molecules, however their solubility is a little less good than that of the second generation molecules (0.3 mM in 100% water). However that may be, the applicants are now continuing along this path with the description of a novel type of molecules which are much more soluble than the third generation molecules (solubility lying between 2 and 28 mM in 100% water) and of a stability equal to or better than that of the molecules already described in our previous inventions.

These four documents disclosed above present the previous three generations of molecules, which are all based on the presence of a diazomethyl function close to a ring. The reader is invited to refer to these four documents for any complementary explanation which may, by unintended omission, be missing in the text disclosing the present invention.

For that, the new invention proposes the introduction of a pyridine nucleus alpha to the diazomethyl function, the recognition group being either in the alpha' position, or on the pyridyl ring (see FIG. 2, molecule 10 or molecule 19).

The fourth generation molecules propose the best profile combining stability and solubility.

This confers on the molecule:
1) chemical stability greater than or equal to that of Nitro DKBs, in dry form at 4° C. or in solution at ambient temperature. This characteristic derives from the electron-attracting effect of the pyridine nucleus which stabilises the diazo function in a remarkable manner, as did the nitro aryl group of the third generation molecules.
2) much greater solubility thanks to the presence of a nitrogen atom on the pyridine nucleus.
3) reactivity with nucleic acids better than the commercial methods for labelling nucleic acids.

The present invention is a considerable improvement on the existing molecules. In fact the first and second generation molecules have the disadvantages of being chemically unstable, even though this aspect was already improved compared to what existed before. Thus the labelling remains very effective as the results obtained are very good even after storage at +4° C. for a year. Further, their synthesis remains relatively complex. The third generation molecules are much more stable and easier to synthesise which presents considerable advantages in terms of the expiry date of kits containing these molecules and the industrialisation of the syntheses.

The first and second generation molecules are functionally stable for one year if they are stored at low temperature in an anhydrous organic solvent. The third generation molecules are much more stable functionally and chemically whether in a liquid medium or in the dry form. They can thus be manipulated in aqueous media after having been stored dry, for example by drying or lyophilisation, for a much longer period (between 10 and 100 times longer), which is not the case with the first or second generation molecules which are unstable during the lyophilisation stage.

This industrial upgrading of the third generation molecules is particularly important in integrated devices or microsystems, where the chemistry deployed has to be very effective and robust without having to adversely affect the stability of certain reagents in the event of a problem.

Finally, the said first and second generation molecules are poorly soluble in an aqueous solution, which is a nuisance for the user who has to solubilise these molecules properly before initiating a reaction.

However, even if these molecules and labelling processes are effective, with their third generation of novel molecules, and novel processes for labelling such molecules which further improve the labelling efficacy, the applicants succeeded in finding a solution to the problem of the stability of the first and second generation molecules.

However, whatever the generation, one to three, of these molecules, another problem lies in their lack of solubility. Thus two new molecular functionalities have been combined to create these novel reagents. They are defined as follows:

the diazomethyl function possesses in the alpha position a pyridine ring, which can itself be singly or multiply substituted with one or more groups in the meta, para or ortho position.
the diazo function can:
as in the third generation molecules, possess in the alpha' position the group enabling detection; this group can be biotin or any other detectable group.
not bear the detectable group, which as in the first and second generation molecules is borne by the ring, in other words the pyridine ring, in the present case.

It should be noted that the fourth generation molecules are as stable and reactive as the third generation molecules, but that their solubility is improved owing to the presence of a pyridine nucleus which likewise stabilises the diazomethyl function owing to its electron-attracting effect.

The term "multimeric structure" is intended to mean a polymer formed of repeat units of chemical or biological synthons. An example is mentioned in Example 34.2 of patent application WO-A-02/090319. Many variants of such structures are known, such as:
linear polymers (EP-A-0 561 722, EP-A-0 669 991),
branched polymers (WO-A-01/92361),
particles (EP-A-0 827 552),
dendrimers (U.S. Pat. No. 4,507,466; U.S. Pat. No. 4,568, 737; U.S. Pat. No. 6,083,708),
polynucleotides, and
polypeptides.

The term "detectable label" is intended to mean at least one label capable of directly or indirectly generating a detectable signal. A non-limiting list of these labels includes:
enzymes that produce a detectable signal, for example by colorimetry, fluorescence, or luminescence, such as horseradish peroxidase, alkaline phosphatase, β-galactosidase, and glucose-6-phosphate dehydrogenase,
chromophores, such as fluorescent, luminescent, and dye compounds,
groups with an electron density detectable by electron microscopy or by virtue of their electrical property, such as conductivity, amperometry, voltametry, and impedance,
detectable groups, for example the molecules of which are sufficiently large to induce detectable modifications of their physical and/or chemical characteristics; this detection can be carried out by optical methods such as diffraction, surface plasmon resonance, surface variation or contact angle variation, and physical methods such as atomic force spectroscopy and the tunnel effect, and
radioactive molecules such as $^{32}P$, $^{35}S$, and $^{125}I$.

Indirect systems may also be used, such as ligands capable of reacting with an anti-ligand. The ligand/anti-ligand pairs are well known to those skilled in the art, which is the case, for example, of the following pairs: biotin/streptavidin, hapten/antibody, antigen/antibody, peptide/antibody, sugar/lectin, and polynucleotide/sequence complementary to the polynucleotide. In this case, it is the ligand that bears the diazomethyl reactive function. The anti-ligand can be directly detectable by means of the labels described in the above paragraph or can itself be detectable by means of another ligand/anti-ligand pair. This stacking system is illustrated in the examples of WO 2005/092910.

Another example of indirect systems uses a specific covalent bond between the ligand and the anti-ligand, for example methyl ketone and alkoxyamine. Examples of this system are described in patent applications WO-A-00/40590 and WO-A-98/05766. These indirect detection systems can produce, under certain conditions, an amplification of the signal and reference may be made to patent applications WO-A-00/07982, WO-A-01/92361, and WO-A-95/08000 for examples of chemical amplification using polymers, or to application WO-A-01/44506 for systems of chemical amplification by stacking.

It is preferable to work with fluorophors for which the excitation wavelength is greater than 450 nm, preferably greater than 600 nm. The definitions of other labels of interest, "conjugation", "enzymatic amplification technique", "homogeneous solution", "solid support" and "purification stage" are given in the patent application WO-A-2005/092910, and the reader is invited to refer to this in case of need.

Likewise, the techniques of:
grafting chemistry, and
the introduction of phosphate at the 3' or 5' terminus of nucleic acids,
are also described in that aforesaid patent application and the reader can find in that document all information necessary for the complete understanding of the present invention.

Further, the diazomethyl function borne by these third generation molecules, as in the first and second generation molecules, makes it possible to graft the nucleic acids onto the support covalently. The grafting is simple and the linkage is stable, in particular compared to adsorption, and makes it possible to effect coupling of the nucleic acid onto the solid support, which facilitates the subsequent hybridisation stages all the more by decreasing the steric hindrance.

This novel family of molecules, described as fourth generation, is called Pyridine Diazo Ketone Biotin (PyDKB) or Pyridine Diazo Biotin (PyDB) and is represented by the relatively temperature-stable labelling reagent respectively of formula (C) for the PyDKB and of formula (D) for the PyDB (see below).

According to a first implementation mode, the present invention proposes a labelling reagent of formula (C):

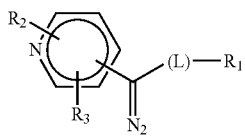

in which:
$R_1$, represents a detectable label or at least two detectable labels linked together by at least one multimeric structure,
$R_2$ and $R_3$ independently of each other represent: H, $NO_2$, Cl, Br, F, I, OR, SR, $NR^2$, R, NHCOR, CONHR, COOR with R=alkyl or aryl, and
L is a linking arm comprising a linear chain of at least two covalent bonds.

According to a second implementation mode, the present invention proposes a labelling reagent of formula (D):

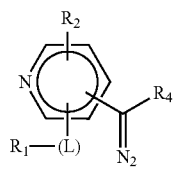

in which:
$R_1$, represents a detectable label or at least two detectable labels linked together by at least one multimeric structure,
$R_2$ represents: H, $NO_2$, Cl, Br, F, I, OR, SR, $NR^2$, R, NHCOR, CONHR, COOR with R=alkyl or aryl,
$R_4$ represents: H, an alkyl group or an aryl group, and
L is a linking arm comprising a linear chain of at least two covalent bonds.

The location of the arm simultaneously bearing the label $R_1$ and the diazomethyl function (formula C) is at the para, meta or ortho position relative to the position of the nitrogen atom of the pyridine nucleus. Preferably, this arm is in the para position relative to the position of the nitrogen of the pyridine nucleus.

The location of the arm bearing the label $R_1$ or the location of the arm bearing the diazomethyl function (formula D) are, independently of each other, in the para, meta or ortho position relative to the position of the nitrogen atom of the pyridine nucleus. Preferably, the arm bearing the diazomethyl function is in the para position relative to the position of the nitrogen atom of the pyridine nucleus, whereas the said arm bearing the label $R_1$ is in the ortho position relative to the position of the said nitrogen atom of the pyridine nucleus.

Preferably, $R_2$ and/or $R_3$ are in the meta position relative to the diazo function. This position allows the conjugation of the diazomethyl function with a substituent $R_2$ and/or $R_3$.

In the sense of the present invention, alkyl group is understood to mean: a saturated aliphatic hydrocarbon group containing from one to six carbon atoms (advantageously one to two, one to three or one to four carbon atoms) which is linear or, when the alkyl chain comprises at least three carbon atoms, branched or cyclic. As examples, the methyl, ethyl, propyl, isopropyl, butyl, isobutyl, tert-butyl, methylcyclopropyl, pentyl, 2'2-dimethylpropyl, hexyl, cyclopropyl, cyclobutyl, cyclopentyl or cyclohexyl groups may be cited.

In the sense of the present invention, aryl group is understood to mean a monocyclic aromatic group, for example a phenyl group.

According to a first modification of the first implementation mode, the present invention proposes a labelling reagent of formula (E):

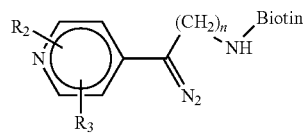

in which:
$R_2$ and $R_3$ independently of each other represent: H, $NO_2$, Cl, Br, F, I, OR, SR, $NR^2$, R, NHCOR, CONHR, COOR with R=alkyl or aryl, and
n is a whole number lying between 1 and 12, preferably between 1 and 6.

According to a first modification of the second implementation mode, the present invention proposes a labelling reagent of formula (F):

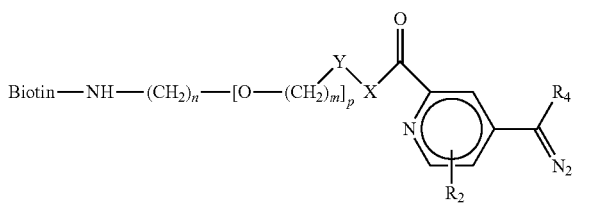

in which:
R$_2$ represents: H, NO$_2$, Cl, Br, F, I, OR, SR, NR$^2$, R, NHCOR, CONHR, DOOR with R=alkyl or aryl,
R$_4$ represents: H, an alkyl group or an aryl group,
—Y—X— represents —CH$_2$NH—, —CONH—, —NHCO—, —CH$_2$O— or —CH$_2$S—, and
m, n and p are each, independently of each other, a whole number lying between 1 and 12, preferably between 1 and 6.

According to a second modification of the first implementation mode, the present invention proposes a labelling reagent of formula (G):

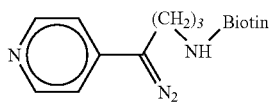

According to a second modification of the second implementation mode, the present invention proposes a labelling reagent of formula (H):

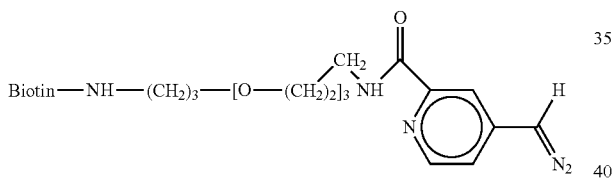

Whatever the implementation mode or even modification thereof, the reagent, according to the invention disclosed above, preferably contains a radical R$_1$ which is made up of a D-biotin residue of formula (I):

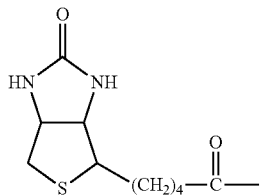

The present invention also relates to a process for synthesis of a labelling reagent, as disclosed above, comprising the following stages (molecule of the PyDKB type):
a) an aromatic carboxylic acid derivative is reacted with the enolate of a lactone (Claisen type reaction) to form a cyclic precursor,
b) which cyclic precursor is then opened with a halo acid to form an aromatic halo ketone,
c) the carbonyl function of the aromatic halo ketone is protected by a protective group to form a protected precursor,
d) which protected precursor is subjected to an amination reaction (of the Gabriel type) to form an aminated precursor,
e) which aminated precursor is deprotected to liberate the amine function, the said amine function being reacted with a detectable label the carboxyl function whereof is activated to form a precursor containing a detectable label,
f) the labelled precursor is subjected to a reaction of deprotection of the carbonyl function to form a labelled and carbonyl-containing precursor and finally
g) the labelled and carbonyl-containing precursor is transformed into a labelling reagent, such as described above, by transformation of the carbonyl function into a diazo function.

As regards the synthesis of molecules of the PyDB type, the stages are as follows:
a) an aromatic dicarboxylic acid is esterified to form a diester,
b) this diester is regioselectively substituted with a compound derived from mono-protected aminated ethylene glycol to form a precursor protected on the carboxyl function and the amine function,
c) which precursor is then reduced to the alcohol and oxidised to the aldehyde,
d) the aldehyde synthesised in stage c) is subjected to an acid treatment in order concomitantly to protect this function while deprotecting the amine function, to lead to an aminated acetal,
e) which aminated acetal is reacted with a detectable label the carboxyl function whereof is activated to form a precursor containing a detectable label,
f) the labelled precursor is subjected to a reaction of deprotection of the carbonyl function to form a labelled and carbonyl-containing precursor, and finally
g) the labelled and carbonyl-containing precursor is transformed into a labelling reagent, such as described above, by transformation of the carbonyl function into a diazo function by a Bamford Stevens type reaction.

The present invention further relates to a process for the labelling of a biological molecule, in particular a nucleic acid, comprising the contacting of a biological molecule and a reagent in homogeneous solution, in an appreciably aqueous buffer. The term "biological molecule" is intended to mean a compound that has at least one recognition site allowing it to react with a target molecule of biological interest. By way of example of biological molecules, mention may be made of nucleic acids, antigens, antibodies, polypeptides, proteins, and haptens.

The term "nucleic acid" means a chain of at least two deoxyribonucleotides or ribonucleotides optionally comprising at least one modified nucleotide, for example at least one nucleotide comprising a modified base, such as inosine, methyl-5-deoxycytidine, dimethylamino-5-deoxyuridine, deoxyuridine, diamino-2,6-purine, bromo-5-deoxyuridine, or any other modified base allowing hybridization. This polynucleotide can also be modified at the level of the internucleotide bond, such as for example, phosphorothioates, H-phosphonates or alkyl phosphonates, or at the level of the backbone, such as, for example, alpha-oligonucleotides (FR 2 607 507) or PNA (M. Eghohn et al., J. Am. Chem. Soc., 114, 1895-1897, 1992) or 2'-O-alkyl riboses. The nucleic acid can be natural or synthetic, an oligonucleotide, a polynucleotide, a nucleic acid fragment, a ribosomal RNA, a messenger RNA, a transfer RNA, or a nucleic acid obtained by means of an enzymatic amplification technique, such as:

PCR (Polymerase Chain Reaction), described in patents U.S. Pat. No. 4,683,195, U.S. Pat. No. 4,683,202 and U.S. Pat. No. 4,800,159, and its derivative RT-PCR (Reverse Transcription PCR), in particular in a one-step format, as described in patent EP-B-0.569.272, [0150] LCR (Ligase Chain Reaction), disclosed, for example, in patent application EP-A-0.201.184, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, TMA (Transcription Mediated Amplification) with patent U.S. Pat. No. 5,399,491, and RCA (Rolling Circle Amplification (U.S. Pat. No. 6,576, 448).

The invention also proposes a labelled molecule capable of being obtained by the process of labelling a biological molecule disclosed above.

The present invention also relates to a process of labelling and fragmentation of a single or double strand nucleic acid comprising the following stages:
fragmenting the nucleic acid,
attaching a label onto at least one of the fragments by means of a labelling reagent selected from the reagents, this reagent coupling covalently and mainly onto at least one phosphate of the said fragment. Such a technique for attachment to the phosphate is, for example, shown in FIG. 1.

According to a first implementation modification, the process is characterized in that the fragmentation and the labelling are effected in two stages.

According to a second implementation modification, the process is characterized in that the fragmentation and the labelling are effected in one stage.

Whatever the implementation modification, the process is characterized in that the labelling is effected in an appreciably aqueous homogeneous solution. The term "appreciably aqueous solution" is intended to mean a solution containing at least 50% of water. This solution preferably contains salts, such as a buffer solution.

Whatever the implementation modification, the process is characterized in that the fragmentation is effected by enzymatic, physical or chemical means.

The processes described above enable the applicants also to claim a labelled nucleic acid capable of being obtained by these processes.

The present invention further relates to a kit for detection of a target nucleic acid containing a labelled nucleic acid, as described above.

The present invention also relates to a solid support onto which is attached a reagent, as described above.

Finally, the present invention relates to a process for capture of nucleic acids comprising the following stages:
a solid support is used onto which there is attached directly or indirectly at least one biological molecule as described above, or a nucleic acid as described above, the biological molecule or the nucleic acid containing a diazomethyl function,
this is contacted with a biological sample capable of containing free nucleic acids, and
the solid support where the molecule(s) are covalently attached to at least one nucleic acid is washed.

These fourth generation DKB molecules bear a spacer arm L, called a linker, and a label $R_1$ which could be constituted of a detectable group, such as, biotin, an hapten, a fluorophor, a fluorescent group, a luminescent group, etc.

L is a linking arm comprising a linear chain of at least two covalent bonds and n a whole number equal to 1. Advantageously and whatever the aforesaid implementation mode or modification of the reagent, L contains an —(O—CH$_2$—CH$_2$)— moiety, repeated from 1 to 20 times, preferably from 1 to 12 times and still more preferably from 2 to 6 times.

The appended examples and figures represent particular implementation modes and cannot be regarded as limiting the scope of the present invention.

Figure 1:
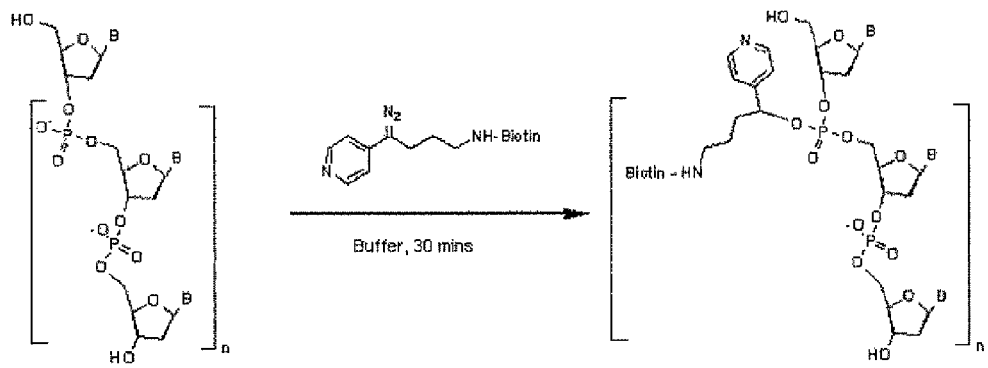
FIG. 1 represents a reaction scheme showing the labelling of a single strand nucleic acid, whether it be in the form of RNA or DNA, by a molecule according to the invention.

In the figures and in the description, the terms "relative fluorescence" and "RFU" are identical.

In the examples given below, the following abbreviations will be used:
Ar: aromatic,
s: singlet,
bs: broad singlet,
d: doublet,
dd: double doublet,
t: triplet,
q: quadruplet,
qu: quintuplet,
m: mound,
M: multiplet,
HPLC: high performance liquid chromatography,
TLC: thin film chromatography,
NMR: nuclear magnetic resonance,
Yld: yield,
Eq: equivalents
Rf or TR: retention time,
DMSO-d6: deuterated dimethyl sulphoxide,
DMCF: dimethyl cyclohexylammonium formate, CDCl₃: deuterated chloroform, and
DMF: dimethylformamide,
DCM: dichloromethane,
MeOH: methanol,
ACN: acetonitrile,
AcOEt: ethyl acetate,
MilliQ water: ultrapure water (Millipore, Molsheim, France),
DMAC: dimethylamino cinnamaldehyde,
Si60: silica gel 60 FLUKA (40-63 μm),
UV: ultraviolet.

The general conditions for the analysis and synthesis of the chemical compounds described (Examples 1, 2, 3, 4 and 9) are:

Equipment:
HPLC conditions (System HPLC WATERS Alliance 2795, diode array detector PDA 996, software Empower version 2 and column WATERS XTerra MS C18 4.6×30 mm, 2.5 μM) with a flow rate of 1 ml/minute at 30° C. (detection at 260 nm).

HPLC Basic Method:
Eluent A: milliQ water
Eluent B: ACN
Eluent C: 500 mM aq. ammonia, pH 12
Namely a linear gradient from 1 to 64% acetonitrile (constant 5 mM of aq. ammonia at pH=9) in 20 minutes.

HPLC Neutral Method:
Eluent A: water milliQ
Eluent C: ACN
Eluent D: 500 mM solution ammonium formate, pH 7
Namely a linear gradient from 1 to 64% C in a 10 mM solution of ammonium formate in 20 minutes.

Synthesis:
The thin layer chromatography analyses were performed on ALUGRAM® MACHEREY-NAGEL SIL G/UV₂₅₄ 4×8 cm (Duren, Germany) silica plates with UV detection at 254 nm or by DMAC for the biotinylated products.

The products were purified by chromatography on Silica gel 60 FLUKA (40-63 μm). The conditions for separation by "flash" chromatography (under argon pressure) strictly observe the conditions described by Clark Still et al (Clark Still, W.; Kahn, M.; Mitra, A. *J. Org. Chem.* 1978, 43, 2923-2925) namely a fixed height of silica of 15 cm pressurised to a flow rate of
5 cm/minute, the diameter of the column depending on the quantity and the Rf of the products to be purified.

For Example 1, the NMR spectra were recorded on a Brüker 200 MHz spectrometer. The chemical shifts (δ) are given in ppm relative to the solvent peak taken as the internal reference (CDCl₃: 7.24 ppm; DMSO-d6: 2.49 ppm; D₂O: 4.80 ppm at 25° C.) The spectra are described with the above abbreviations: s, d, t, q, qu, m and M. The coupling constants (J) are expressed in hertz (Hz).

For Example 2, the ¹H and ¹³C NMR spectra were run on Bruker AC 200 or Bruker DPX 300 spectrometers at ambient temperature. The chemical shifts (δ) are expressed in ppm relative to tetra-methylsilane and calibrated relative to CHCl₃ ($\delta_H$=7.27, $\delta_C$=77.0) or DMSO ($\delta_H$=2.52, $\delta_C$=40.0). The coupling constants (J) are expressed in hertz (Hz). The shape of the signals is abbreviated as follows: bs and dd.

Mass Spectra:
The mass spectra (SM) were obtained with an LCQ-ion trap instrument (Thermofinnigan, San Jose, Calif., USA) by Electrospray ionisation methods in positive mode by infusion through a silica tube at 2 to 10 μL/minute. The main solvents used are DCM and MeOH.

EXAMPLE 1

Synthesis of Pyridine Diazo Biotin (PyDB)

Objective:
To demonstrate the feasibility of the synthesis of a molecule containing a pyridine nucleus alpha to a diazomethyl function, and a recognition group on the aromatic ring, according to the reaction scheme disclosed below:

Procedure:

Dimethylpyridine-2,4-dicarboxylate (2)

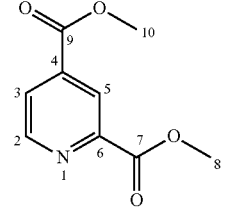

PCl₅ (39 g; 0.186 mol; 3 eq) and pyridine-2,4-dicarboxylic acid (11.5 g; 6.2×10⁻² mol) are introduced into a 500 mL flask. The mixture is stirred at ambient temperature for 45 minutes: it forms a green liquid. It is then diluted with dichloromethane (80 mL) then methanol is added (20 mL) with caution. The whole is poured into water H₂O (300 mL) containing 60 g of NaHCO₃, the aqueous phase is washed with dichloromethane (4×50 mL) and the organic phase is washed with 1M Na₂CO₃ (2×50 mL). The crude product is purified by flash chromatography (eluent: 75:25 AcOEt/cyclohexane).

Solid: m=11.71 g
Yield: 96%
Storage: ambient temperature

¹H NMR (200 MHz, CDCl₃): 4.03 (s, 3H, —OMe); 4.09 (s, 3H, —OMe); 8.07 (dd, J=6 Hz, 1H, H₃); 8.68 (s, 1H, H₅); 8.91 (d, 1H, H₂)

¹³C NMR (75 MHz, CDCl₃): 53.28 (C₈, C₁₀); 124.49 (C₅); 126.29 (C₃); 138.64 (C₄); 149.06 (C₆); 150.92 (C₂); 162.45 (C₇); 164.96 (C₉)

Methyl 2-{N-[13-(t-butoxycarbonylamino)-4,7,10-trioxa-tridecyl]aminocarbonyl}pyridine-4-carboxylate (3)

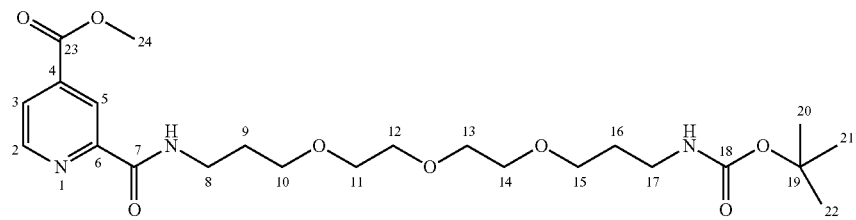 [SMILES: COC(=O)c1ccnc(C(=O)NCCCOCCOCCOCCCNC(=O)OC(C)(C)C)c1]

The diester 2 (2.25 g; $1.1 \times 10^{-2}$ mol) in toluene (3 mL) is introduced into a 25 mL flask. The Boc-diamine (3.7 g; $1.2 \times 10^{-2}$ mol; 1.1 eq) is added then the mixture is stirred at 90° C. for 20 hours. The toluene is evaporated then the crude mixture is purified by flash chromatography (eluent gradient: 10, 20 and 30% dichloromethane/acetone).

Transparent oil: m=2.9 g
Yield: 55%
Storage: ambient temperature $^1$H NMR (300 MHz, CDCl$_3$): 1.42 (s, 9H, -Boc); 1.74 (q, 2H, H$_9$); 1.92 (q, 2H, H$_{16}$); 3.21 (q, 2H, H$_8$); 3.61 (m, 16H, H$_{10}$-H$_{11}$-H$_{12}$-H$_{13}$-H$_{14}$-H$_{15}$-H$_{17}$); 3.97 (s, 3H, —OMe); 5.01 (m, 1H, N—H); 7.96 (d, 1H, H$_5$); 8.35 (s+d, 2H, H$_3$+H$_2$); 8.69 (m, 1H, N—H)

$^{13}$C NMR (75 MHz, CDCl$_3$): 28.63 (C$_{20}$-C$_{21}$-C$_{22}$); 29.30 (C$_{16}$); 29.74 (C$_9$); 37.55 (C$_{17}$); 38.85 (C$_8$); 53.02 (C$_{24}$); 69.69 (C$_{10}$-C$_{15}$-C$_{11}$-C$_{14}$); 70.78 (C$_{12}$-C$_{13}$); 79.97 (C$_{19}$); 121.60 (C$_5$); 125.52 (C$_3$); 139.08 (C$_4$); 149.23 (C$_2$); 151.76 (C$_6$); 156.27 (C$_{18}$); 163.65 (C$_7$); 165.60 (C$_{23}$)

4-(Hydroxymethyl)pyridine-2-N-[13-(t-butoxycarbonylamino)-4,7,10-trioxamidecyl]-carboxamide (4)

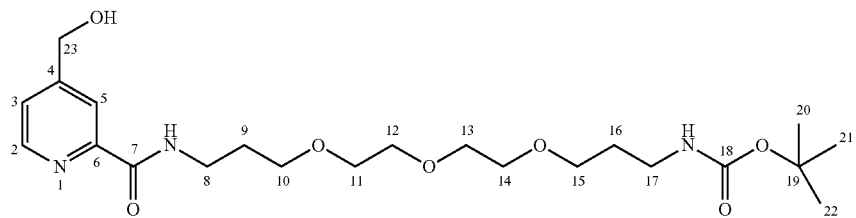 [SMILES: CC(C)(C)OC(=O)NCCCOCCOCCOCCCNC(=O)c1cc(CO)ccn1]

The monoester (2.73 g; $5.4 \times 10^{-3}$ mol) is dissolved in MeOH (20 mL) in a 250 mL flask. The mixture is cooled by means of an ice bath, and NaBH$_4$ (1.32 g; $3.5 \times 10^{-2}$ mol; 6.5 eq) is added little by little. The mixture is stirred for 30 minutes at ambient temperature.

The mixture is diluted in H$_2$O (100 mL) and neutralised with saturated NH$_4$Cl then extracted with dichloromethane (4×100 ml.). The organic phases are combined, evaporated and dried under vacuum in the desiccator for one night.

Transparent oil: m=2.44 g
Yield: 95%
Storage: ambient temperature $^1$H NMR (200 MHz, CDCl$_3$): 1.42 (s, 9H, -Boc); 1.75 (q, 2H, H$_9$); 1.91 (q, 2H, H$_{16}$); 3.02 (m, 15, OH); 3.19 (q, 2H, H$_8$); 3.59 (m, 16H, H$_{10}$-H$_{11}$-H$_{12}$-H$_{13}$-H$_{14}$-H$_{15}$-H$_{17}$); 4.79 (d, 2H, H$_{23}$); 5.03 (m, 1H, N—H); 7.47 (d, 1H, H$_3$); 8.15 (s, 1H, H$_5$); 8.39 (m, 1H, N—H); 8.51 (d, J=5 Hz, 1H, H$_2$)

$^{13}$C NMR (75 MHz, CDCl$_3$): 28.77 (C$_{20}$-C$_{21}$-C$_{22}$); 29.26 (C$_{16}$); 30.07 (C$_9$); 37.68 (C$_{17}$); 39.01 (C$_8$); 63.70 (C$_{23}$); 69.42 (C$_{10}$-C$_{15}$); 70.39 (C$_{11}$-C$_{14}$-C$_{12}$-C$_{13}$); 79.96 (C$_{19}$); 119.95 (C$_5$); 123.87 (C$_3$); 148.44 (C$_2$); 150.03 (C$_6$); 143.34 (C$_4$); 156.42 (C$_{18}$); 164.96 (C$_7$)

4-(Formyl)pyridine-2-N-[13-(t-butoxycarbonylamino)-4,7,10-trioxamidecyl]carboxamide (5)

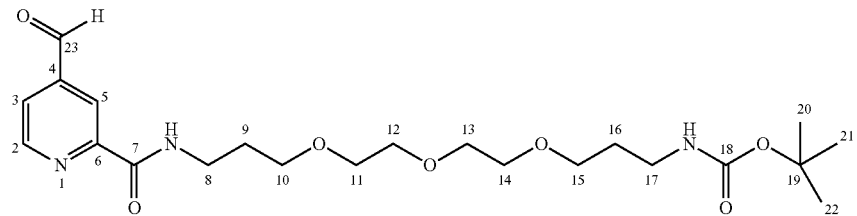 [SMILES: CC(C)(C)OC(=O)NCCCOCCOCCOCCCNC(=O)c1cc(C=O)ccn1]

(COCl)$_2$ (1.2 mL, 13.7 mmol) in solution in dichloromethane (5 mL) is added to a solution of DMSO (2.0 mL, 28.2 mmol) in dichloromethane (8 mL) at −70° C. under argon. This is left for 30 minutes with stirring at −70° C. then the alcohol 4 (1.92 g, 4.2 mmol) in solution in dichloromethane (20 mL) is added dropwise. This is left for 30 minutes with stirring at a temperature of −70° C., and NEt$_3$ (6.5 mL, 47 mmol) is added. The reaction mixture is stirred at 0° C. for 3 hrs, then poured into water (70 mL). The aqueous phase is extracted with the said dichloromethane, washed (NaHCO$_3$), dried over MgSO$_4$ and evaporated to give a viscous oil. Liberation of Me$_2$S then takes place, hence sodium hypochlorite solution must be used to trap this and to wash contaminated vessels. The crude product is purified by flash chromatography (eluent: 85:15 AcOEt/acetone).

Transparent oil:
m=1.46 g
Yield: 75%
$^1$H NMR (300 MHz, CDCl$_3$): 1.42 (s, 9H, -Boc); 1.76 (q, J=6 Hz, 2H, H$_9$); 1.95 (q, J=6 Hz, 2H, H$_{16}$); 3.22 (q, 2H, H$_8$); 3.57 (m, 16H, H$_{10}$-H$_{11}$-H$_{12}$-H$_{13}$-H$_{14}$-H$_{15}$-H$_{17}$); 4.98 (m, 1H, N—H); 7.85 (d, 1H, H$_3$); 8.59 (s, 1H, H$_5$); 8.77 (d, 1H, H$_2$); 10.15 (s, 1H, H$_{al}$)
$^{13}$C NMR (75 MHz, CDCl$_3$): 29.59 (C$_{20}$-C$_{21}$-C$_{22}$); 30.03 (C$_9$-C$_{16}$); 38.11 (C$_8$-C$_{17}$); 70.11 (C$_{10}$-C$_{15}$); 70.99 (C$_{11}$-C$_{14}$-C$_{12}$-C$_{13}$); 79.50 (C$_{19}$); 122.27 (C$_5$); 123.68 (C$_3$); 143.22 (C$_4$); 149.80 (C$_2$); 152.61 (C$_6$); 156.35 (C$_{18}$); 163.62 (C$_7$); 191.32 (C$_{23}$)

4-(Dimethoxymethyl)pyridine-2-N-(13-amino-4,7, 10-trioxatri-decyl)-carboxamide (6)

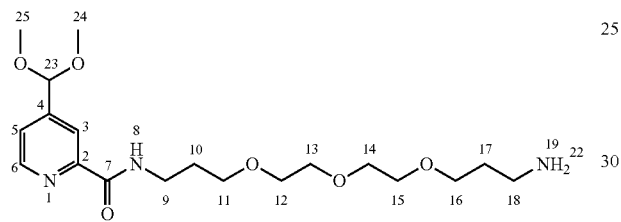

The aldehyde 5 (1.4 g, 3.1 mmol, 1 eq) is dissolved in 10 mL of methanol. TMSCl (1 mL, 7.9 mmol, 2.5 eq) is added and the mixture is stirred overnight. A 1M solution of sodium hydroxide (40 mL) is added and the product is extracted with dichloro-methane, the organic phases are dried in presence of sodium carbonate and the solvent is evaporated under vacuum.

M=997 mg
Yield: 81%
$^1$H NMR (300 MHz, CDCl$_3$): 8.54 (d, 1H, H$_6$), 8.35 (br s, 1H, H$_8$), 8.24 (s, 1H, H$_3$), 7.52 (d, 1H, H$_5$), 5.42 (s, 1H, H$_{23}$), 3.71-3.53 (m, 15H, H$_9$+H$_{11-16}$), 3.33 (s, 6H, H$_{24}$, H$_{25}$), 2.80 (t, 2H, H$_{18}$), 1.91 (quint, 2H, H$_{10}$), 1.75 (quint, 2H, H$_{17}$)

Acetal-Biotin (7)

The acetal (6) (1.54 g, 3.9 mmol) is dissolved in 30 mL of dichloromethane. Biotin (1.36 g, 4.2 mmol, 1.1 eq) is added and the mixture is stirred for two hours. The solution is extracted three times with 50 mL of 1M sodium carbonate. The aqueous phases are washed with 50 mL of dichloromethane. The organic phase is dried over magnesium sulphate and the solvent is evaporated. The crude product is purified by flash chromato-graphy: SiO$_2$, Φ=50 mm, 15 cm. Eluent: 700 mL 10% methanol/dichloromethane and then 1 L 15% methanol/dichloro-methane. Next the solvent is evaporated, and the oily residue is washed with ether. A white powder is obtained.

m=1.78 g
Yield: 74%
$^1$H NMR (300 MHz dual, CDCl$_3$): 8.55 (d, 1H, H$_2$), 8.35 (t, 1H, H$_{13}$), 8.26 (s, 1H, H$_5$), 7.55-7.53 (m, 1H, H$_1$), 6.7 (broad s, 1H, H$_{42}$), 6.2 (broad s, 1H, H$_{40}$), 5.44 (s, 1H, H$_7$), 4.4-4.6 (m, 1H, H$_{38}$), 4.2-4.4 (m, 1H, H$_{39}$), 3.71-3.54 (m, 16H, H$_{15}$, H$_{17-25}$, H$_{27}$), 3.34 (s, 6H, H$_{10-11}$), 3.2-3.1 (m, 1H, H$_{35}$), 3-2.8 (m, 1H, H$_{37}$), 3.8-3.7 (m, 1H, H$_{37'}$), 2.19 (t, 2H, H$_{31}$), 1.92 (quint, 2H, H$_{16}$), 1.8-1.3 (m, 8H, H$_{26}$, H$_{32-34}$).

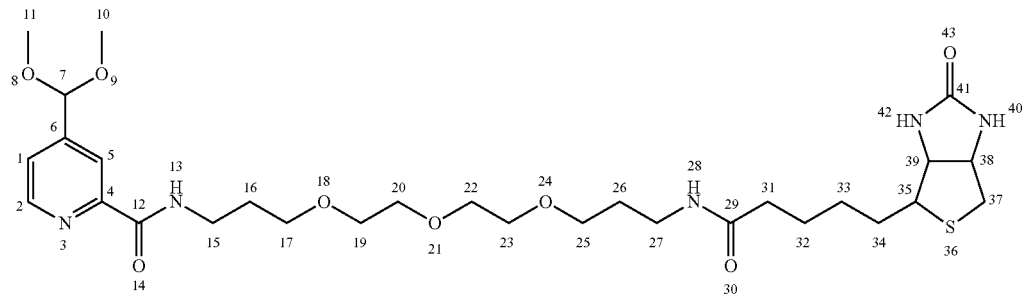 [SMILES: COC(OC)c1ccnc(C(=O)NCCCOCCOCCOCCCNC(=O)CCCCC2SCC3NC(=O)NC32)c1]

Aldehyde (8)

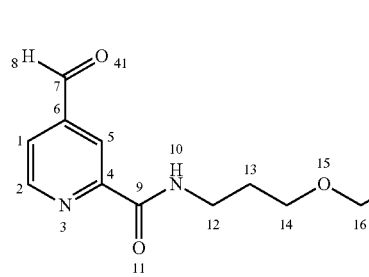

The acetal (7) (1.76 g, 2.8 mmol) is dissolved in an 80:20 acetic acid/water solution (20 mL) and the mixture is stirred at 60° C. for 24 hours under argon. The solution is evaporated and the oily residue is washed with ether until a white powder is obtained.

M=1.83 g

Yield: about 100%

$^1$H NMR (300 MHz dual, DMSO-d6): 10.17 (s, 1H, H$_8$), 8.92 (s+d, 2H, H$_{10,2}$) 8.42 (s, 1H, H$_5$), 7.99 (d, 1H, H$_1$), 7.73 (t, 1H, H$_{25}$) 6.4-6.3 (s+ broad s, 2H, H$_{39,37}$), 4.3-4.1 (m+m, 2H, H$_{35,36}$), 3.53-3.28 (m, 18H, H$_{12,14-22,24}$), 3.07 (m, 1H, H$_{32}$), 2.80 (d, 1H, H$_{34}$), 2.78 (d, 1H, H$_{34'}$), 2.2-1.00 (m, 12H, H$_{13,28-31}$).

Φ=30 mm, 15 cm, eluent: 10% methanol/dichloromethane. The oily residue is washed with ether until a yellow powder is obtained.

M=1.57 g

Yield: 75%

$^1$H NMR (300 MHz dual, DMSO-d6): 12.0 (broad s, 1H, H$_{39}$), 8.83 (s, 1H, H$_8$), 8.63 (d, 1H, H$_2$), 8.13 (s, 1H, Hu), 7.99 (s, 1H, H$_5$) 7.77 (d, 2H, H$_{46,50}$), 7.69 (d, 1H, H$_1$), 7.42 (d, 2H, H$_{47,49}$), 6.41 (s, 1H, H$_{37}$), 6.35 (s, 1H, H$_{35}$), 4.4-4.2 (m, 1H, H$_{34}$) 4.0-4.2 (m, 1H, H$_{33}$) 3.51-3.33 (m, 16H, H$_{9,11-20,22}$), 3.1-3.0 (m, 2H, H$_{32}$), 2.8-2.7 (m, 1H, H$_{30}$), 2.36 (s, 3H, H$_{51}$), 2.03 (t, 2H, H$_{10}$), 1.77 (t, 2H, H$_{21}$) 1.6-1.2 (m, 8H, H$_{26-29}$).

Tosylhydrazone (9)

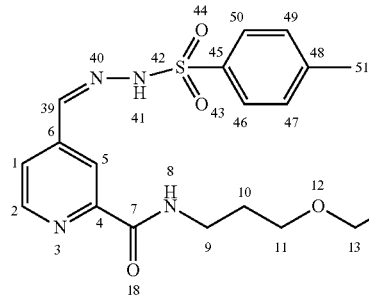

A solution of aldehyde 8 (1.62 g, 2.79 mmol) in dimethylformamide (20 mL) is stirred at 130° C. for 30 minutes under argon. 4-methylbenzenesulphonhydrazide is added and the mixture is stirred for one hour. The solvent is evaporated and the crude product is purified by flash chromatography: SiO$_2$,

Final Diazo Compound (10)

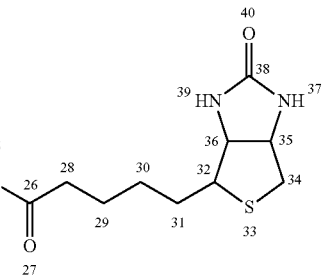

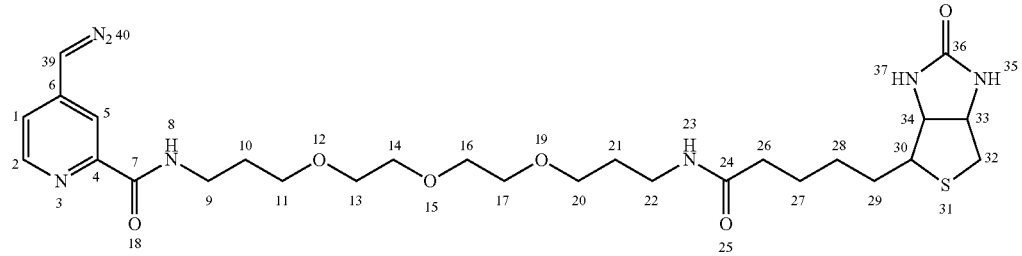

The tosylhydrazone 9 (200 mg, 0.27 mmol) is introduced into a mL flask. A solution of sodium hydride (60% in oil) (42.8 mg, 1.07 mmol, 4 eq) in methanol (10 mL) is added and the mixture is left for 24 hours with stirring at ambient temperature. The product is extracted with 10 mL of 0.5M $Na_2CO_3$ and 4×10 mL of dichloromethane. The oily residue is washed with ether. An orange powder is obtained.

M=135 g

Yield: 88%

$^1$H NMR (200 MHz dual, $CDCl_3$): 8.31-8.28 (br s+d, 2H, $H_{8,2}$), 7.73 (d, 1H, $H_5$), 6.88 (dd, 1H, $H_1$), 6.62 (t, 1H, $H_{23}$), 6.13 (s, 1H, $H_{37}$), 5.32 (s, 1H, $H_{35}$), 5.10 (s, 1H, $H_{39}$), 4.6-4.4 (m, 1H, $H_{34}$), 4.4-4.2 (m, 1H, $H_{33}$), 3.7-3.5 (m, 18H, $H_{9,11-20,22}$), 3.13 (m, 1H, $H_{30}$), 2.88 (dd, 1H, $H_{32}$), 2.72 (d, 1H, $H_{32'}$), 2.2-1.3 (m, 12H, $H_{10,21,26-29}$).

Results and Conclusions:

We have demonstrated that the synthesis of a compound containing a diazomethyl function conjugated with a pyridine nucleus bearing a recognition group (biotin) was feasible in good yield.

EXAMPLE 2

Synthesis of Pyridine Diazo Ketone Biotin (PyDKR)

Objective:

To demonstrate the feasibility of the synthesis of a molecule containing a pyridine nucleus alpha to a diazo function and a recognition group (biotin) alpha prime to the diazo function according to the reaction scheme below.

Procedure:

Synthesis of the Bromo Ketone (12)

γ-Butyrolactone (5.020 g/4.55 ml; 32.23 mmol; 1.0 eq) is diluted in THF (15 ml; 3.3 v) then cooled to 0° C. in an ice bath. Sodium hydride (60%; 3.018 g; 75.42 mmol; 2.27 eq) is added in portions in the space of 5 minutes then the ice bath is withdrawn for 30 minutes. The flask is returned to 0° C. then ethyl isonicotinate (3.80 ml; 49.84 mmol; 1.5 eq) in solution in THF (245 ml; 64.5 v) is run in drop by drop. The reaction is stirred for 18 hours at ambient temperature. The THF is removed by evaporation under vacuum then the residue is taken up in 100 ml of ethyl ether, the expected product precipitates, and the suspension is filtered, then dried on the rotary evaporator at 1 mbar for 20 minutes to give a product. Some of the product (4.721 g; 24.7 mmol) is taken up in 48% hydrobromic acid (38 ml that is 650 mM) in water then brought up to 110° C. for 2 hours. The reaction mixture is basified to pH 9 with $Na_2CO_3$ then made up with 200 ml of water and extracted twice with 200 ml of ethyl acetate. The organic phase is dried over $Na_2SO_4$, filtered through cotton and evaporated on the rotary evaporator.

m=3.096 g

Yield (over the 2 stages): 21%

HPLC method: neutral

Synthesis of the Protected Bromo Ketone (13)

In a 500 mL flask, the bromo ketone (3.096 g; 13.57 mmol; 1.0 eq) is dissolved in anhydrous methanol (165 ml; 80 mM) to which trimethylsilyl chloride is added (51.5 ml; 407.2 mmol; 30.0 eq) then the reaction mixture is placed under argon before heating to 53° C. (temperature lower than the boiling point of the reagents) for 18 hours. The reaction mixture is evaporated to dryness then taken up in 50 ml of water and basified to pH 9-10 with 35% caustic soda solution then made up to 200 ml and extracted with 2×150 mL of dichloromethane (also abbreviated as DCM). The organic phase is dried over $Na_2SO_4$ filtered and evaporated to dryness under reduced pressure. The evaporation residue is taken up in 1 mL of DCM and placed on a column of normal phase Si60 silica gel (h=5 cm; diam.=15 cm; eluent: DCM/MeOH: 95/5).

m=1.506 g

Yield: 40%

TLC eluent: DCM/MeOH: 95/5

HPLC method: neutral $^1$H NMR (200 MHz, $CDCl_3$): δ=1.4 to 1.7 (M; 2H; e); 3.0 to 3.25 (m; 8H; f,g); 3.30 (t; 2H; d); 7.42 (d; 2H; a); 8.65 (d; 2H; b).

Protected Aminated Ketone (Gabriel Reaction) (15)

The bromo ketone (1.506 g; 5.49 mmol; 1.0 eq), potassium phthalimide (1.526 g; 8.24 mmol; 1.5 eq) and DMF (55 ml 0.1 M) are introduced into a 100 mL flask, then heated for 15 minutes at 155° C. The solvent is evaporated to dryness, then the evaporation residue is taken up in 200 ml of a 100 mM caustic soda solution and extracted with 2×200 mL of DCM, and the dichloromethane phase is dried over $Na_2SO_4$ filtered, and evaporated to dryness to give the compound 14. The whole of this (5.49 mmol; 1.0 eq) is reacted with 25% hydrazine in water (21.35 ml; 109.8 mmol; 20 eq) and methanol (109 ml; 50 mM), and the reaction mixture is stirred for 18 hours. The solvents are removed then the residue is taken up in 200 ml of a 10 mM solution of caustic soda then extracted with 3×200 mL of DCM. The organic phase is dried over $Na_2SO_4$ filtered and evaporated under reduced pressure, then the oil obtained is taken up in 1 mL, of DCM and placed on a column of normal phase Si60 silica gel (h=15 cm; diam.=3 cm; eluent: DCM/MeOH/$NH_3$: 97.5/2.5/1).

m=300 mg
Yield: 26%
TLC eluent: DCM/MeOH/NH₃: 90/10/1
HPLC method: neutral
¹H NMR (phthalimide 14) (200 MHz, CDCl₃): δ=1.2 to 1.3 (M; 2H; e); 1.88 (M; 2H; d); 3.03 (t; 6H; g); 3.44 (dd; 2H; f); 7.45 (d; 2H; a); 7.57 to 7.71 (m; 4H; i and j); 8.52 (d; 2H; b).
¹H NMR (amine 15) (200 MHz, CDCl₃): δ=1.0 to 1.2 (m; 4H; e and f); 1.88 (M; 2H; d); 2.54 (t; 2H; h); 3.15 (t; 6H; g); 7.35 (d; 2H; a); 8.58 (d; 2H; b).

Synthesis of the Activated Biotin (20)

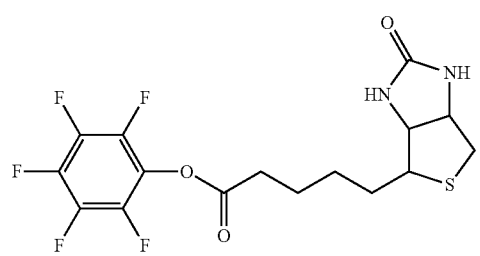 [SMILES: O=C1NC2CSC(CCCCC(=O)Oc3c(F)c(F)c(F)c(F)c3F)C2N1]

Biotin (5 g; 23.1 mmol; 1.0 eq) is suspended in anhydrous DMF (50 ml) and pyridine (2.07 ml; 25.4 mmol; 1.1 eq). After stirring for 5 minutes, pentafluorophenyl trifluoroacetate (PFP-TFA: 4.621 ml, i.e. 7.50 g; 25.4 mmol; 1.1 eq) is added. After stirring for one night, the reaction is finished, and the solvents are evaporated on the rotary evaporator. The evaporation residue is taken up in 100 ml of ethyl ether to suspend it, then filtered off on a fritted filter, and the cake is rinsed with a minimum of ether. Note: in the TLC a small trace of biotin is observed, but that will have no impact on what follows.
m=7.106 g
Yield: 81%
TLC eluent: DCM/MeOH: 90/10

Coupling Between Biotin and the Aromatic Amine (Compound 16)

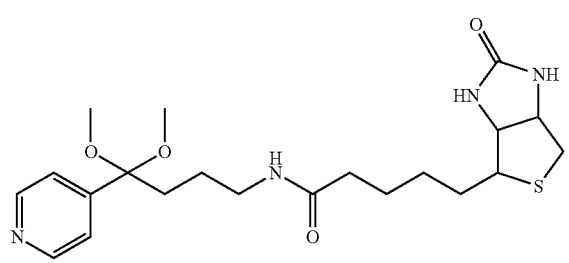 [SMILES: COC(CCCNC(=O)CCCCC1SCC2NC(=O)NC21)(OC)c1ccncc1]

The compound 15 (808 mg; 2.0 mmol; 1.4 eq) is dissolved in DMF (4.28 ml) at 60° C., before addition of triethylamine (1.60 ml; 11.4 mmol; 8.0 eq) after 5 minutes' stirring. The compound 20 in solution in DMF (2.85 ml at 500 mM, i.e. 300 mg; 1.4 mmol; 1.0 eq) is incorporated all at once. After 60 minutes, the solvent is evaporated under reduced pressure. No further processing is performed, and the crude reaction product is used directly for deprotection.
The mass and yield will be calculated in the following stage.
HPLC method: neutral Biotinylated Ketone (Compound 17)

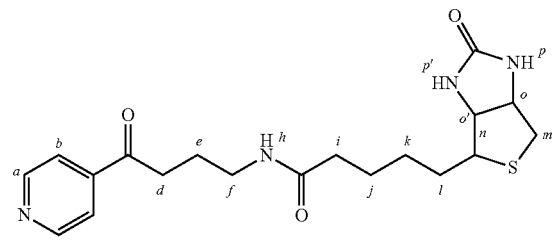 [SMILES: O=C(CCCCC1SCC2NC(=O)NC21)NCCCC(=O)c1ccncc1]

The compound 16 is taken up in 50 ml of a 6M solution of hydro-chloric acid and stirred for 2 hours at ambient temperature. The solution is evaporated to dryness; the residue is a red oil in the form of hydrochloride. It is taken up in a 90/8/2 DCM/MeOH/TEA mixture, the oil decolourises and a gas is evolved, 2 mL of triethylamine are added then the mixture is evaporated to dryness to give a precipitate which is taken up in 100 ml of ethyl ether and 10 mL of DCM, the suspension is filtered and the cake is triturated with 50 ml of ether before being placed in the oven under vacuum for 2 hours at 28° C. The powder is taken up in 5 mL of 88/12 DCM/MeOH mixture to which 250 µl of 2M caustic soda solution are added to dissolve it all. This solution is placed on a silica gel Si60 column of diameter 3 cm, h=16 cm v=5 cm/minute, which is eluted with an 88/12 DCM/MeOH mixture.
m=940 mg
Yield: 83% over two stages, and if no account is taken of the 2.9 eq of triethylamine hydrochloride.
TLC eluent: DCM/MeOH: 85/15.
HPLC method: neutral
¹H NMR (200 MHz, DMSO): δ=1.28 (t; TEA); 1.49 (M; 2H; k); 1.30 to 1.50 (m; 4; j and l); 1.73 (quint; 2H; e); 2.05 (t; 2H; i); 2.6 to 2.8 (M; 2H; m); 2.9 to 3.2 (m; 5H+H of TEA; d, f, n and TEA); 4.0 to 4.3 (m; 2H; o and o'); 6.38 (s; 1H; p'); 6.43 (s; 1H; p); 7.78 (d; 2H; b); 7.95 (t; 1H; h); 8.08 (d; 2H; a); 10.3 (M; TEA hydrochloride).

Hydrazonation of the Ketone (18)

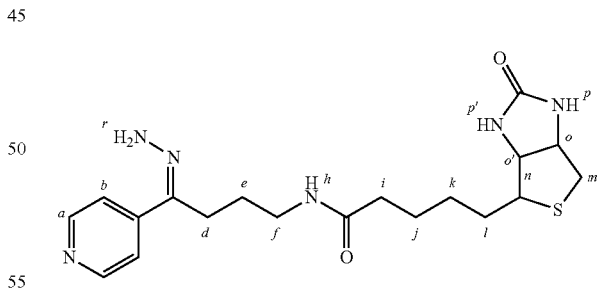

The ketone 17 (400 mg; 506.5 µmol) is dissolved in DMF (2.25 ml; 224 mM), MeOH (11.3 ml; 44.8 mM) and acetic acid (580 µl; 10.13 mmol; 20 eq) before addition of 247 µl of hydrazine monohydrate (246 µL; 5.065 mmol; 10 eq). The solution is stirred for two hours then evaporated to dryness.
The evaporation residue is taken up in 5 ml of water then transferred into a 15 ml flask before then being basified with 2M caustic soda until a pH of 10 is reached, the product precipitates, and the tube is stirred by vortex so as to mix well, then centrifuged at 8000 rpm. The supernatant is discarded then the operation is repeated twice more taking 5 ml of a pH 10 caustic soda solution. The precipitate (yellow powder) is dried in an oven under vacuum at ambient temperature before being used in the oxidation stage.

m=190 mg
Yield: 93%
HPLC method: neutral then basic.
$^1$H NMR (200 MHz, DMSO): δ=1.2 to 1.7 (m; 8H; e, j, k and l); 1.73 (quint; 2H; e); 2.06 (t; 2H; i); 2.6 to 2.9 (M; 2H; m); 3.0 to 3.2 (m; 3H; f and n); 4.10 to 4.35 (m; 2H; o and o'); 6.39 (s; 1H; p'); 6.47 (s; 1H; p); 7.11 (s; 2H; r); 7.55 (d; 2H; b); 7.87 (t; 1H; h); 8.47 (d; 2H; b).

Biotinylated Pyridine Diazo Ketone (PyDKB) (19)

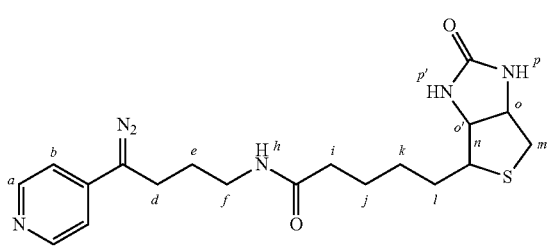

The hydrazone 18 (177.2 mg; 438 µmol; 1.0 eq) is partially dissolved in DMF (22 ml; 20 mM) before being cooled to 0° C. for the addition of tetramethylguanidine (448 µl; 3.56 mmol; 8.14 eq), 3 Å molecular sieve (722 mg; 3.8 times the mass of the reagent taken) and manganese oxide (2.387 g; 35.6 mmol; 81.4 eq). The suspension is stirred for 20 minutes, then filtered on a 1 cm thick celite plug, and the plug is rinsed with methanol until the filtrate runs colourless. The solution is evaporated to dryness then taken up in 20 mL of 90/10 DCM/MeOH and washed with a 0.25 M solution of $Na_2CO_3$. A precipitate is formed. After analysis, the precipitate and the organic phase are combined and evaporated to dryness in order to be dissolved in 100 mL of 90/10 DCM/MeOH mixture and washed with 100 mL of 0.05 M $Na_2CO_3$. The organic phase is recovered, dried over anhydrous $Na_2CO_3$, filtered and evaporated to dryness.

m=42.8 mg
Yield: 24.3%
HPLC method: basic.
$^1$H NMR (200 MHz, DMSO): δ=1.20 to 1.74 (m; 8H; e, j, k and l); 1.73 (quint; 2H; e); 2.07 (t; 2H; i); 2.6 to 2.9 (M; 2H; m); 3.00 to 3.25 (m; 3H; f and n); 4.10 to 4.35 (m; 2H; o and o'); 6.37 (s; 1H; p'); 6.44 (s; 1H; p); 6.94 (d; 2H; b); 7.90 (t; 1H; h); 8.35 (d; 2H; b).

Results and Conclusions:
We have demonstrated that the synthesis of a compound containing a diazomethyl function conjugated with a pyridine nucleus in the alpha position and linked to a recognition group (biotin) at alpha' is feasible in good yield.

EXAMPLE 3

Demonstration of the Stability of PyDB or PyDKB Relative to a Molecule of BBP (bis-bio-PRAM) in a Liquid Medium at Ambient Temperature Objective:
The objective is to demonstrate the stability of the PyDB or PyDKB molecules in a liquid medium in comparison to a second generation molecule. For this, an accelerated stability study is performed under extreme conditions where the compounds are stored at 125 mM in a 96/4 DMSO/methanol mixture at ambient temperature (22° C.+/−1° C.). It should be noted that these are extreme storage conditions.

Figure 2:
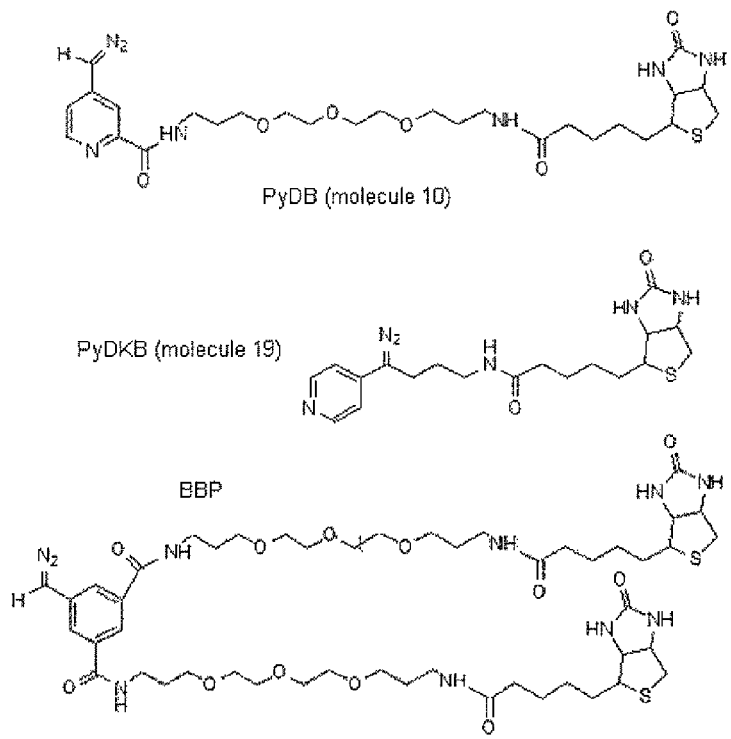
FIG. 2 is a summary of the molecules used in the present patent application.
Figure 3:
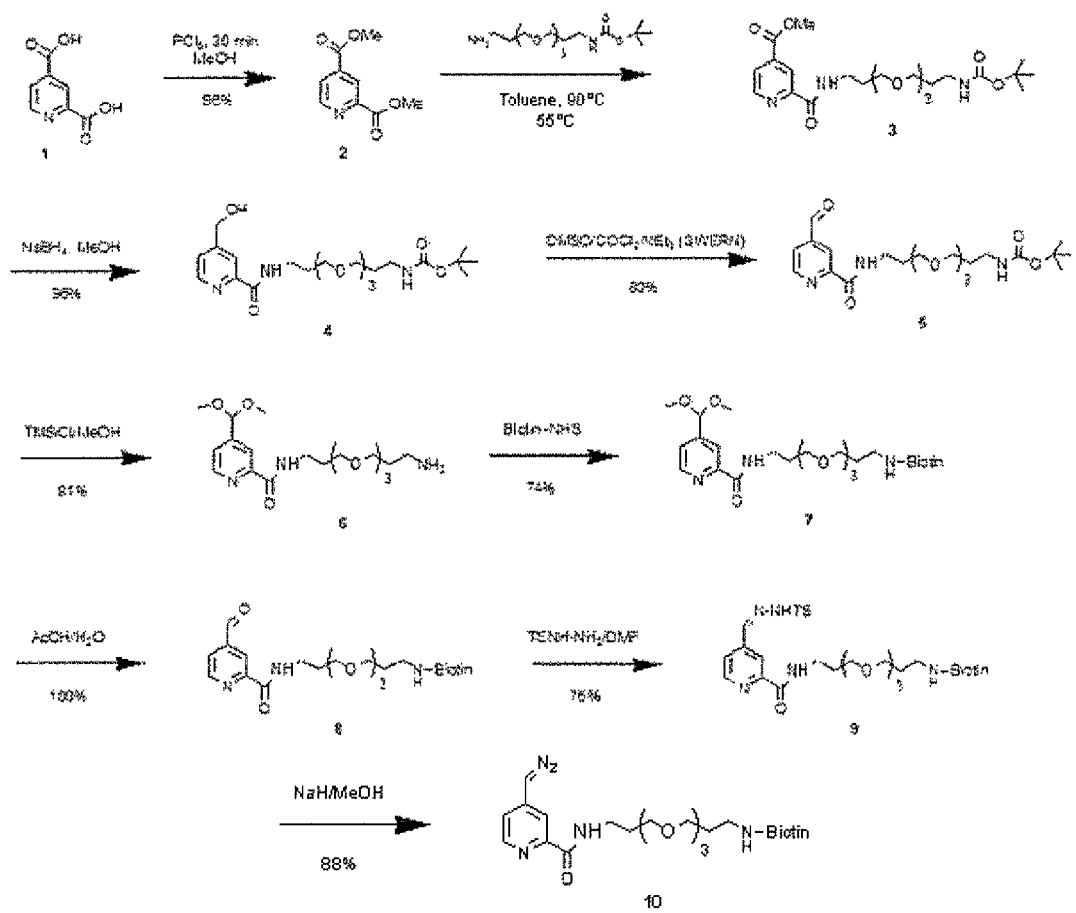
FIG. 3 represents a reaction scheme of the process of synthesis of a molecule of PyDB (molecule 10).
Figure 4:
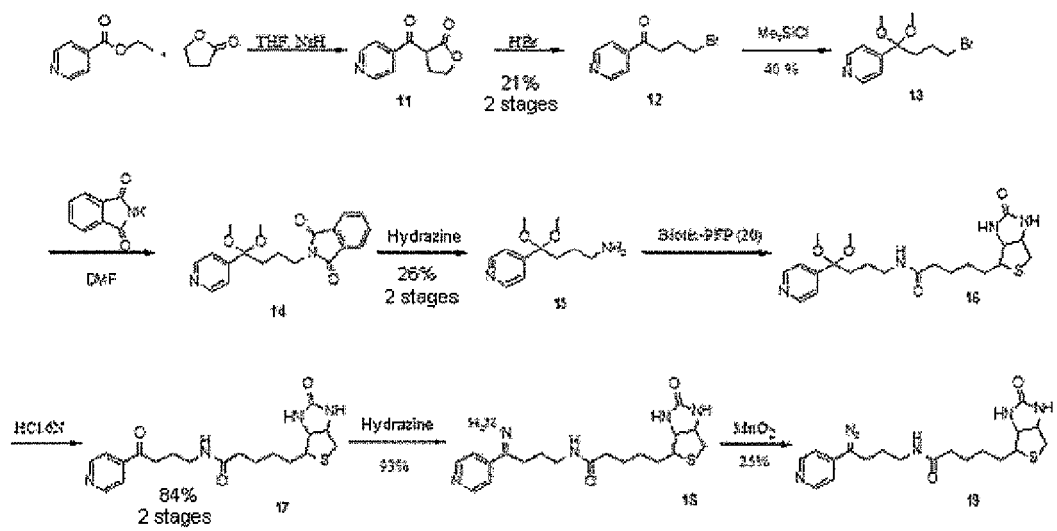
FIG. 4 represents a reaction scheme of the process of synthesis of a molecule of PyDKB (molecule 19).
Figure 5:
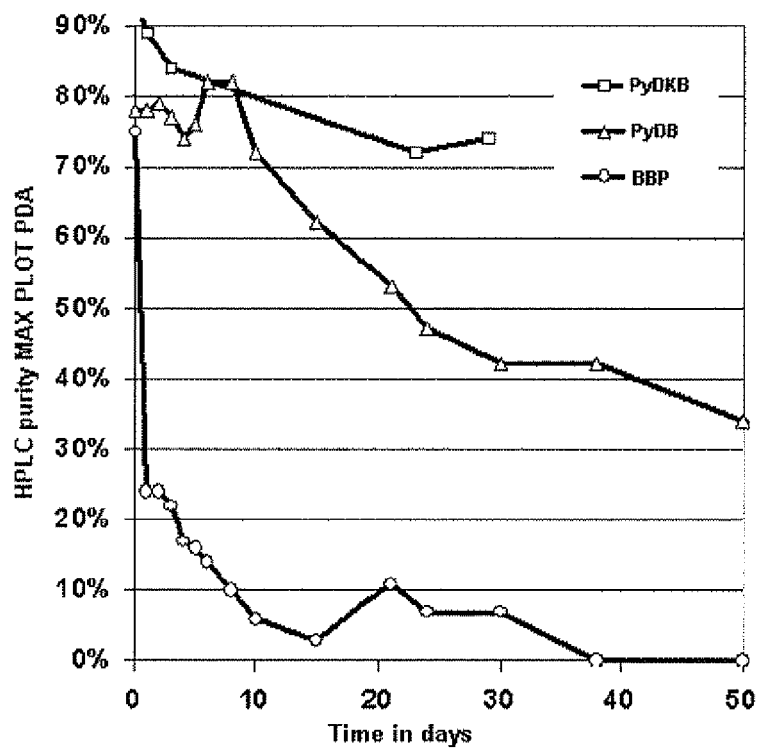
FIG. 5 represents the stability, compared in a liquid medium, of the molecules PyDB and PyDKB relative to a second generation [Bio-EG3]2-PDAM (hereinafter referred to as BBP) molecule, described in the application WO-A-02/090319.

Procedure:
The three compounds PyDB, PyDKB and BBP, shown in FIG. 2, are dissolved at 125 mM in a 96/4 DMSO/methanol mixture and stored at ambient temperature (22° C. plus or minus 1° C.). 2 µL of these solutions are then injected regularly into an HPLC (basic method, Waters HPLC system) in order to measure the degradation of the main product by integration of the totality of the peaks in the chromatogram (PDA Max Plot on the software Empower 2). The variation in the purity of the initial compound is then plotted as a function of time, as is well shown in FIG. 5.

Results and Conclusions:
It is unambiguously demonstrated that BBP degrades in a few days (<10% purity at 10 days) whereas the two fourth generation molecules PyDB and PyDKB are still stable at more than 80% at the end of this time period.

The presence of the pyridyl moiety alpha to the diazo function stabilises the latter by an electronic delocalisation which renders the diazo function less sensitive to hydrolysis. The presence of the label at alpha' further considerably stabilises this function by rendering it less susceptible to hydrolysis in an aqueous medium.

EXAMPLE 4

Demonstration of the Stability of PyDB Compared to a Molecule of BBP, in the Dry Form at +4° C.

Objective:
To demonstrate the dry stability of the PyDB or PyDKB molecules in comparison to a second generation BBP molecule.

Figure 6:
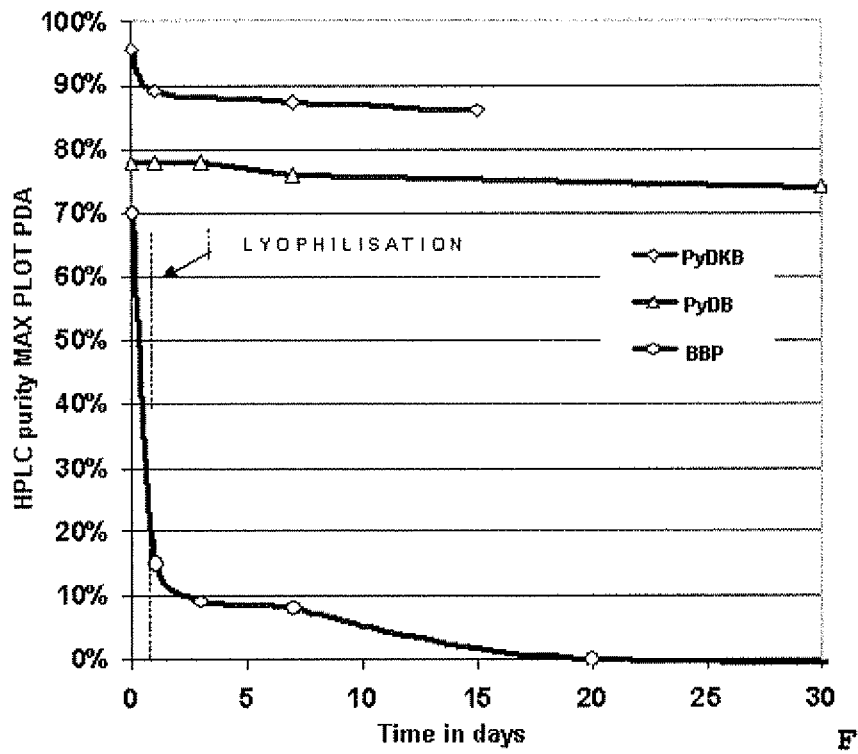
FIG. 6 represents the stability, compared in the dry form, of the two fourth generation molecules PyDB and PyDKB relative to a second generation BBP molecule.
Figure 7:
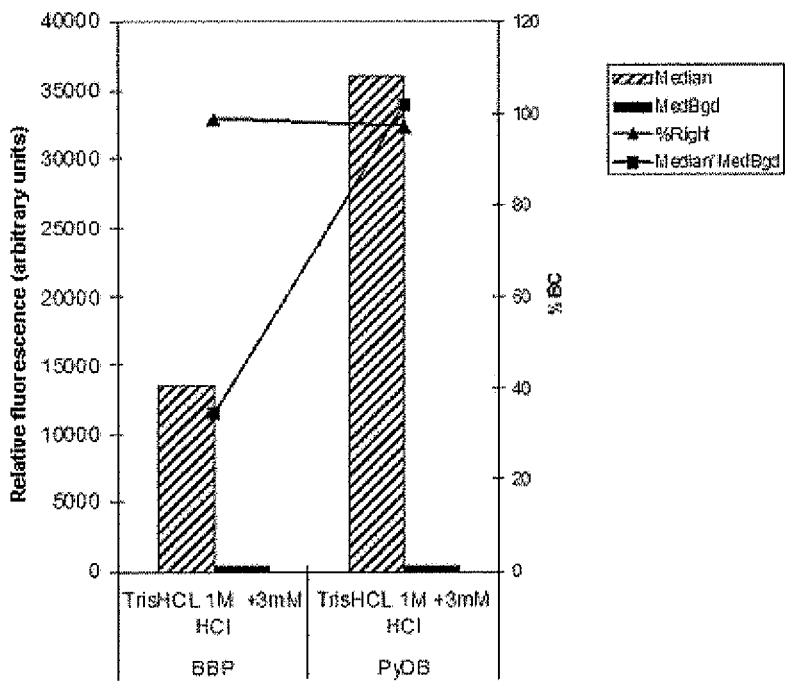
FIG. 7 shows the results of labelling of an RNA amplicon after purification, by means of the labels BBP and PyDB each of the labels being at a concentration of 45 mM.
Figure 8:
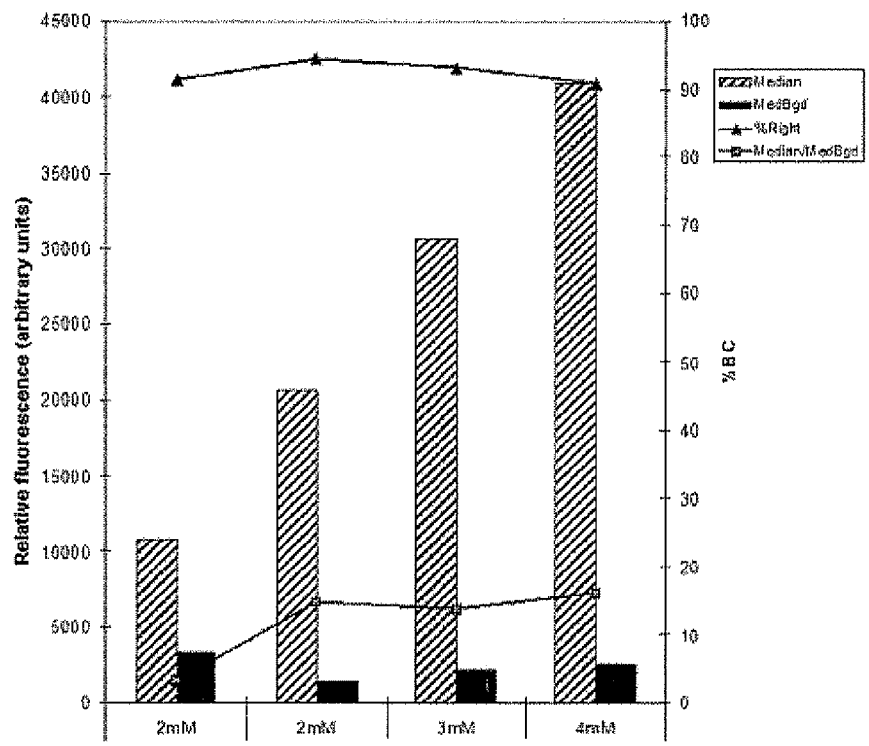
FIG. 8 shows the results of labelling of an RNA amplicon without purification, by means of the labels BBP and PyDB, each of the labels being at a concentration of 2 mM and in presence of 3 mM HCl.

Procedure:
The two PyDB compounds and the BBP are dissolved at 250 mM in a solution of 10 mM Tris HCl pH 7.5 and 10% trehalose. The solutions are lyophilised for one night in 50 nmole aliquots. The dry products are then stored at +4° C. These aliquots are regularly dissolved in methanol and 15 µL of these solutions are injected into an HPLC (Waters) in order to measure the degradation of the main product by integration of the totality of the peaks in the chromatogram (PDA Max Plot on the software Empower). The variation in the purity of the initial compound is then plotted as a function of time, as is well shown in FIG. 6.

Results and Conclusions:
In the same way as in Example 3, but to a still more marked extent, it is demonstrated that BBP does not withstand lyophilisation (>60% degradation for this stage) whereas PyDB and PyDKB remain perfectly stable for this operation. Further, keeping for more than one month in the dry state and at 4° C. shows only very little degradation (more than 80% purity for the two fourth generation labels).

Once again it is demonstrated that the presence of the pyridyl moiety alpha to the diazo function stabilises the latter by an electronic delocalisation which renders the diazo function less sensitive to hydrolysis.

EXAMPLE 5

Labelling of Nucleic Acids with PyDB Compared to a Molecule of BBP with Interim Purification Objective:
To demonstrate the efficacy of the labelling of nucleic acids with a PyDB molecule in comparison to a second generation molecule (BBP).

For this, amplicons of RNA, fragments of the sequence of *Mycobacterium tuberculosis* of 174 bases, derived from an amplification reaction (NASBA, kit NucliSens Basic Kit from bioMérieux B.V.—Boxtel—Netherlands) are labelled with biotin by reaction with diazo labels. The products of the labelling reaction are detected by hybridisation on a DNA chip from Affymetrix (Custom DNA Chip Combo Myco described in J. Clin. Microbial., 37(1), PP49-55, A. Troesch et al., 1999).

Procedure:

In a tube, the following are mixed:

18 μL of 250 mM solution of label (96/4 DMSO/methanol), this being either the PyDB or the BBP, 12 μL of DMSO, 15 μL of NASBA 0.5× buffer (Kit "NucliSens Basic Kit Easy Q bioMérieux"), 35 μL of 1 M Tris HCl, 5 μL of 0.1×NASBA (NASBA amplification reaction diluted tenfold, amplicon of 174 bases), and 15 μL of 20 mM HCl.

The solution is mixed by vortex then incubated for 10 minutes at 65° C.

Purification of the Nucleic Acids:

The labelled nucleic acids were purified on a QiaQuick column (PCR purification kit QiaQuick, Qiagen, Hilden, Germany) using the purification protocol recommended by the manufacturer. The elution volume is 100 μL.

Hybridisation on DNA Chip:

After purification, the labelled nucleic acids are transferred into 400 μL of hybridisation buffer. The samples are hybridised on the DNA chips designed for the analysis of the "GenBank" M20940 sequence of the 16S RNA of *Mycobacterium tuberculosis*. This DNA chip is described by A. Troesch et al., in an article published in J. Clin. Microbial., 37(1), PP49-55, 1999.

The hybridisation stages were performed on FS 450 fluidics stations (Affymetrix, Santa Clara, Calif.) using the hybridisation protocol and the buffers described in the foregoing publication by A. Troesch et al.

The hybridisation is revealed by coupling with streptavidin (SA) labelled with phycoerythrin (PE), which interacts with the biotin of the labels used under the following conditions: 300 μL of pure water; 300 μL of 100 mM Tris buffer pH 7/1 M NaCl/0.05% Tween 20/0.005% antifoamant; 6 μL of BSA (50 mg/mL); 6 μL of SA-PE (300 μg/mL).

Reading of the DNA Chip:

The reading of the fluorescence emitted at the surface of the DNA chip after labelling and hybridisation and the generation of data in terms of signal intensity and percentage homology are performed with the reading systems and software supplied by Affymetrix (Scanner Gene Chip Array and GCOS software). The reading system supplies signal and background noise intensities expressed in rfu ("relative fluorescence unit"). The percentage homology (% BC or % Right in FIG. 7 but also later in FIGS. 8 and 10) is given relative to a reference sequence which in this case is the sequence of *Mycobacterium tuberculosis*.

The results in terms of median signal intensity (Med), background noise (Med Bckgd) and percentage homology (% Right) are given in the graph in FIG. 7 for the labels BBP and PyDB.

In general, it is a percentage homology greater than 90% which is sought as a priority. Secondly, it is a high specific signal and low background noise which are desired.

Results and Conclusions:

This example shows that the label PyDB gives a fluorescent signal three times higher than the signal given by the BBP reference molecule.

Taking account of the very great stability of PyDB, this label demonstrates its superiority in comparison to the molecules of the previous generations.

EXAMPLE 6

Labelling of Nucleic Acids with PyDB Compared to a Molecule of BBP, Without Interim Purification Objective:

The aim is to demonstrate the same thing as in Example 5, but using unfavourable conditions, where the excess label is not removed by purification.

Procedure:

In a 1 mL tube, the following are mixed:

5 μL of 8 mM label solution (96/4 DMSO/Methanol). This is either PyDB or BBP,

5 μL of 0.1×NASBA (Kit NucliSens Basic Kit from bioMérieux),

5 μL of 1M Tris HCl, and

5 μL of 20 mM HCl.

The solution was mixed by vortex then incubated for 10 minutes at 65° C. The nucleic acids thus labelled are not purified, but are hybridised directly.

Hybridisation on DNA Chip:

The labelled nucleic acids are transferred without purification into 480 μL of hybridisation buffer. The samples are hybridised on the DNA chips in the same way as for the previous example.

Reading of the DNA Chip:

The results in terms of intensity, background noise and percentage homology, for the labels BBP and PyDB, are presented in the graph in FIG. 8.

Results and Conclusions:

This example shows that, on account of its structure, the label PyDB displays reduced background noise compared to the reference molecule BBP. The specific signals signifying specific hybridisation are also improved and the percentage homology, relatively low for BBP, becomes higher for PyDB (2 mM).

Once again, the superiority of the fourth generation molecules compared to those of the previous generations is demonstrated.

EXAMPLE 7

Evaluation of the Stability Over 24 Hours of an Amplicon Labelled with PyDB

Objective:

The aim is to demonstrate that a labelled RNA amplicon can be hybridised for up to 24 hours on a DNA chip without losing its fluorescent intensity, which demonstrates the stability of the RNA-Label Bond.

Procedure:

In a tube, the following are mixed:

5 μL of a 10 mM solution of label (PyDB or BBP) in DMSO/MeOH (96/4),

5 μL of NASBA 0.1× (Kit NucliSens Basic Kit from bioMérieux) amplification product, 5 μL of 1 M Tris HCl, and 5 HL of water.

The solution is mixed by vortex then incubated for 10 minutes at 65° C.

Purification of the Nucleic Acids:

The labelled nucleic acids were purified on a QiaQuick (PCR purification kit, Qiagen) column using the purification protocol recommended by the manufacturer. The elution volume is 100 µL.

Hybridisation on DNA Chip:

After purification, the labelled nucleic acids are transferred into 400 of hybridisation buffer. The samples are hybridised on the DNA chips designed for the analysis of the "GenBank" M20940 sequence of the 16S RNA of *Mycobacterium tuberculosis*. This DNA chip is described in the publication by A. Troesch et al., J. Clin. Microbiol., 37(1), PP49-55, 1999. The hybridisation stages were performed by injecting. 80 µL of the hybridisation mixture into the chip then maintaining this in a hybridisation oven at 45° C. for 0.5 hour, 2 hours, 6.5 hours or 24 hours.

The hybridisation is revealed by coupling with streptavidin (SA) labelled with phycoerythrin (PE), which interacts with the biotin of the labels used under the following conditions: 300 µL of pure water; 300 µL of 100 mM Tris buffer pH 7/1 M NaCl/0.05% Tween 20/0.005% antifoamant; 6 µL of BSA (50 mg/mL); 6 µL of SA-PE (300 µg/mL).

Reading of the DNA Chip:

The reading of the fluorescence emitted at the surface of the DNA chip after labelling and hybridisation and the generation of data in terms of signal intensity and percentage homology are performed with the reading systems and software supplied by Affymetrix. The reading system supplies signal and background noise intensities expressed in rfu ("relative fluorescence unit"). The percentage homology is given relative to a reference sequence which in this case is the sequence of *Mycobacterium tuberculosis*.

Figure 9:
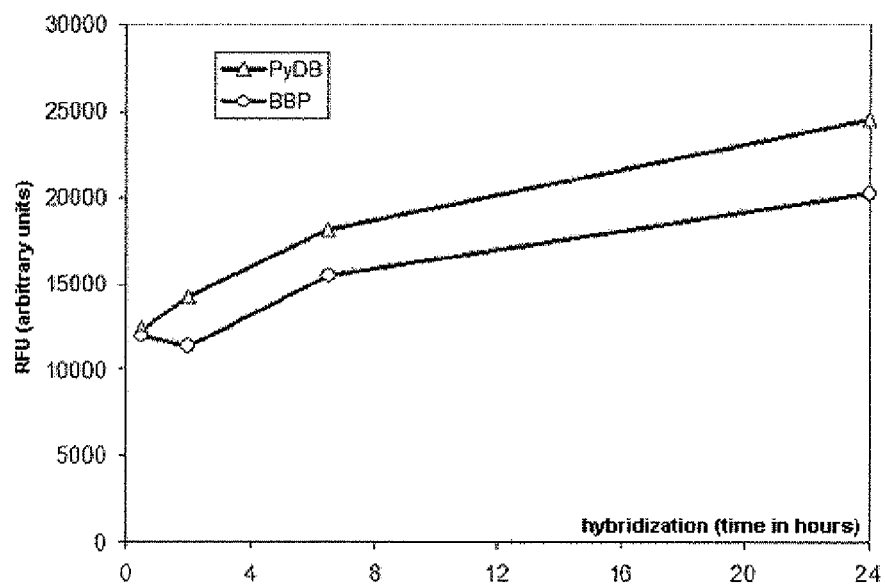
FIG. 9 represents the stability of the labelling of an RNA amplicon labelled with the labels PyDB or BBP, at a concentration of 2.5 mM, over 24 hours of hybridisation.

The results in terms of median signal intensity (Med), as a function of the duration of hybridisation are given in FIG. 9 for the fourth generation label PyDB.

The show that the fluorescence signal remains stable, or even has a tendency to rise as a function of the duration of the hybridisation.

Results and Conclusions:

This example shows that amplicons labelled with PyDB remain perfectly stable in the course of the hybridisation which can be prolonged for 24 hrs (of particular interest for long hybridisations and expression of genes in cancerology), see FIG. 9.

An increase in the fluorescence signal in the course of time is even observed which is due to better hybridisation of the amplicons (the hybridisation kinetics are slow).

The stability of the label-nucleic acid bond is thus demonstrated.

EXAMPLE 8

Comparison of the Efficacy of Labelling of the Molecules Described in the Present Invention Relative to that of a Commercially Available Technology (ULS RNA Labelling Kit)

Procedure:

The RNA amplicons are prepared by a NASBA amplification as before and are labelled with the molecules BBP and PyDB.

In a tube, the following are mixed:
5 µL of 1×NASBA (Kit NucliSens Basic Kit from bioMérieux),
5 µL of 20 mM solution of label (BBP or PyDB) in 96/4 DMSO/Methanol,
5 µL of 1 M Tris HCl pH 7.4 and
5 µL of water.

The solution was mixed by vortex then incubated for 10 minutes at 65° C.

For the labelling with the commercial kit "ULS RNA Labelling Kit" from Kreatech (Amsterdam, Netherlands), the protocol recommended by the supplier was followed. In summary, the following are mixed:
20 µL of 1×NASBA (Kit NucliSens Basic Kit, bioMérieux B.V., Boxtel, Netherlands),
1 µL of label solution,
3 µL 10× buffer, and
6 µL of water.

The solution was incubated for 30 minutes at 85° C.

Purification of the Nucleic Acids:

The nucleic acids labelled by means of the molecules BBP or PyDB were purified on QiaQuick (PCR purification kit, Qiagen) column using the purification protocol recommended by the manufacturer. The elution volume is 100 µL.

For the nucleic acids labelled by means of the commercial kit, ULS RNA Labelling Kit, the purification recommended and supplied by Kreatech (Amsterdam, Netherlands) was used. The final volume is 30 µL, to which are added 100 µL of a blocking solution recommended by that company.

Hybridisation on DNA Chip:

After purification, the labelled nucleic acids are transferred into 400 µL of hybridisation buffer (BBP or PyDB) or 370 µL of Kreatech hybridisation buffer. The said nucleic acids are hybridised on the DNA chips designed for the analysis of the "GenBank" M20940 sequence of the 16S RNA of *Mycobacterium tuberculosis*.

This DNA chip is described in the publication by A. Troesch et al., J. Clin. Microbiol., 37(1), PP49-55, 1999. The hybridisation stages were performed on fluidics stations (Affymetrix FS 450) using the hybridisation protocol and the buffers described in this publication by A. Troesch et al.

The hybridisation is revealed by coupling with streptavidin (SA) labelled with phycoerythrin (PE), which interacts with the biotin of the labels used under the following conditions: 300 µL of pure water; 300 µL of 100 mM Tris buffer pH 7/1 M NaCl/0.05% Tween 20/0.005% antifoamant; 6 µL of BSA (50 mg/mL); 6 µL of SA-PE (300 µg/mL).

Reading of the DNA Chip:

The reading of the fluorescence emitted at the surface of the DNA chip after labelling and hybridisation and the generation of data in terms of signal intensity and percentage homology are performed with the reading systems and software supplied by Affymetrix (Gene Chip Array and GCOS software). The reading system supplies median values of signal (Median) and background noise (MedBgd) intensities expressed in rfu ("relative fluorescence unit"). The percentage homology (% right), also called "base call percentage" (% BC), is given relative to a reference sequence which in this case is the sequence of *Mycobacterium tuberculosis*.

Figure 10:
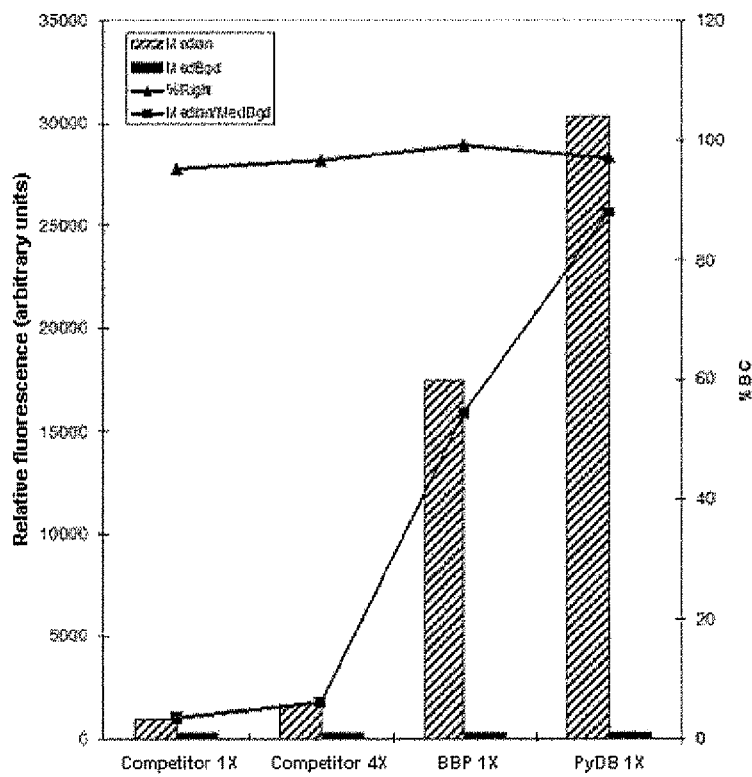
FIG. 10 shows the comparison of the efficacy of labelling of an RNA amplicon depending on the labelling technique used, either ULS (Universal Labelling System) from Kreatech (Amsterdam, Netherlands), or according to the present invention.

The results in terms of median signal intensity (Med), background noise (MedBgd) and percentage homology (% Right or % BC) are given in FIG. 10 for the labels BBP and PyDB and for the competing kit.

Results and Conclusions:

It is found that the technology using cis-platin labels (ULS RNA Labelling Kit), applied exactly under the conditions described by the supplier, has a potential for labelling much inferior to the technical solution provided by the present invention, since with this commercial kit it is necessary to add more than four times the concentration of RNA to have a signal clearly detached from the background noise (Competitor 4×, FIG. 10), but which remains in all cases weaker, ten times weaker than the labelling performed with the BBP molecules and eighteen times weaker than the labelling performed with the PyDB molecules.

In all cases, the percentage identification (4$BC or % Right) remains the same.

Labelling on the internucleoside linkages in comparison to another labelling technique thus makes it possible to obtain a much better detection sensitivity and this whatever the molecule generation. As for the fourth generation, this yet again shows its superiority in this new example.

EXAMPLE 9

Comparison of the Solubility of Two Third Generation Diazo Labels (para Nitro DKB and Meta Nitro DKB) and Two Fourth Generation Labels (PyDB and PyDKB)

Objective:

It is desired to demonstrate that the presence of the pyridine nucleus on a diazo labelling reagent improves the solubility of the molecule.

Procedure:

Determination of the Molar Epsilons (ε) of the Labels:

A few milligrams of label (5-15 mg) are weighed out precisely and dissolved at 100 mM in DMSO (entirely soluble). This solution is diluted to $1/10^{th}$ in MeOH then again to $1/100^{th}$ in MeOH (to $1/1000^{th}$ at the final dilution). The UV spectrum of this solution is measured in order to determine the λmax at which the absorbance is measured. This measurement makes it possible to calculate the molar ε of each label (Beer Lambert law).

Determination of the Solubility of the Labels in Water

A few milligrams of label (5-15 mg) are weighed out precisely and dissolved at 100 mM in water (partially soluble). This is stirred by means of a vortex and centrifuged. The supernatant is removed and diluted to $1/10^{th}$ or $1/100^{th}$ in MeOH. The UV spectra of the labels are measured, making sure that there has been no degradation. The absorbance is measured at the λmax and the concentration of label in the supernatant is calculated using the molar ε value previously determined, that is to say the solubility of the label in water (FIG. 11).

Figure 11:
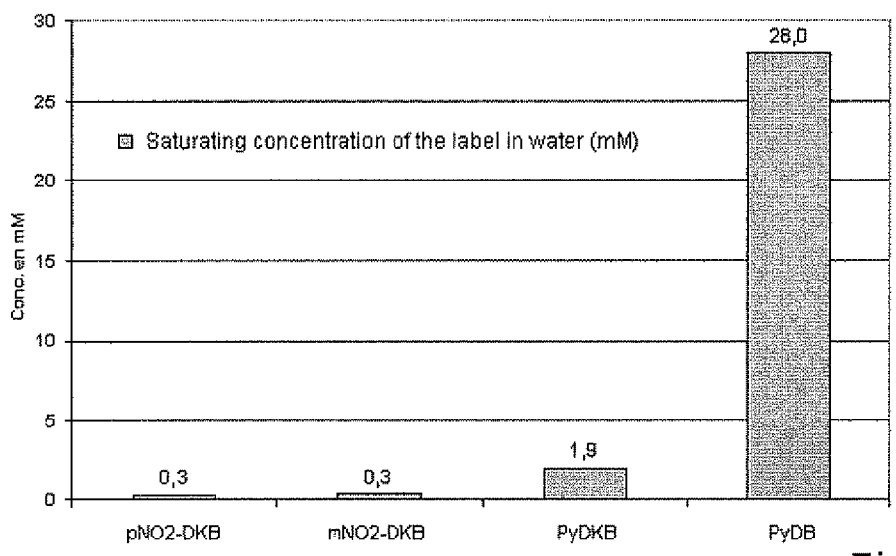
FIG. 11 shows the comparative solubility in an aqueous medium of two third generation molecules (meta Nitro DKB and para Nitro DKB) relative to two fourth generation molecules (PyDB and PyDKB), determined by HPLC.

Results and Conclusions:

It can be seen in FIG. 11 that PyDB is six times more soluble in water than the third generation molecules para Nitro DKB and meta Nitro DKB. This gain in solubility is solely due to the presence of the pyridyl nucleus. PyDB is ninety times more soluble than the third generation molecules para Nitro DKB and meta Nitro DKB. This gain in solubility is also mostly conferred by the disubstituted pyridine nucleus.

We have thus demonstrated the very great impact of the pyridyl nucleus on the final solubility of these molecules.

It is confirmed that the pyridine nucleus is a nucleus known for its basicity, and one could predict a stabilisation of the diazomethyl function but conversely a lack of reactivity towards nucleic acids. In fact the mechanism of the diazo/phosphate reaction is based on a proton exchange. The presence of a proton-trapping nucleus (pyridine) could have inhibited the reaction, but now it has been observed that this phenomenon only appeared with stronger bases such as piperidine. The labelling reaction is performed at pH 7 in a buffered medium.

In the example where the label is at alpha', one could have expected problems of reactivity with the phosphates by reason of increased steric hindrance problems. Here again the effect of these molecules is surprising.

Further, the generation of diastereoisomers during the alkylation of the phosphates risked interfering with the hybridisation and hence the detection of the nucleic acids. This was foreseeable and led one to believe that this type of label would be less effective. It was therefore not obvious to create this type of molecule and to obtain such good labelling results.

The invention claimed is:

1. A labelling reagent of formula (D):

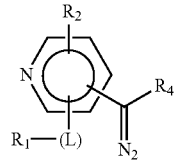

in which:
$R_1$ represents a detectable label or at least two detectable labels linked together by at least one multimeric structure, the detectable label or the at least two detectable labels being independently selected from the group consisting of biotin, fluorophors, fluorescent groups, and luminescent groups, wherein the excitation wavelength of the fluorophors and the fluorescent groups is greater than 450 nm, $R_2$ represents: H, $NO_2$, Cl, Br, F, I, OR, SR, $NR^2$, R, NHCOR, CONHR, or COOR, where R=an alkyl or an aryl group, $R_4$ represents: H, an alkyl group, or an aryl group, and L is a linking arm comprising a linear chain of at least two covalent bonds.

2. The labelling reagent according to claim 1, of formula (F):

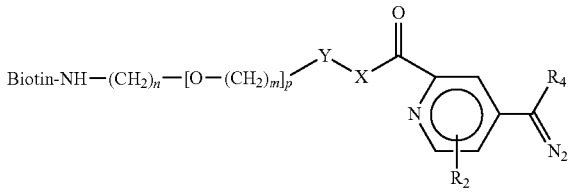

in which:
$R_2$ represents: H, $NO_2$, Cl, Br, F, I, OR, SR, $NR^2$, R, NHCOR, CONHR, or COOR, where R=an alkyl or an aryl group, $R_4$ represents: H, an alkyl group, or an aryl group, —Y—X— represents —$CH_2NH$—, —CONH—, —NHCO—, —$CH_2O$—, or —$CH_2S$—, and m, n and p are each, independently of each other, a whole number lying between 1 and 12.

3. The labelling reagent according to claim 1, of formula (H):

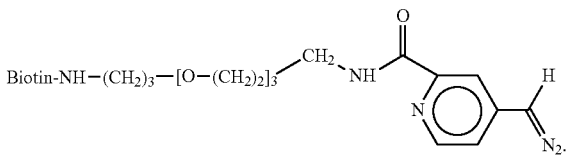

4. The labelling reagent according to claim 1, wherein $R_1$ is a D-biotin residue of formula (I):

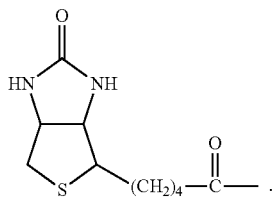

5. A process for synthesizing the labelling reagent according to claim 1, comprising:
   a) esterifying an aromatic dicarboxylic acid to form a diester,
   b) regioselectively substituting the diester with a compound derived from a mono-protected aminated ethylene glycol to form a precursor protected on a carboxyl function and an amine function,
   c) reducing the precursor to an alcohol and then oxidizing the alcohol to an aldehyde,
   d) acid treating the aldehyde to concomitantly protect the aldehyde function while deprotecting the amine function, to form an aminated acetal,
   e) reacting the aminated acetal with a detectable label the carboxyl function whereof is activated to form a precursor containing a detectable label,
   f) deprotecting the carbonyl function of the labelled precursor to form a labelled and carbonyl-containing precursor, and then
   g) transforming the labelled and carbonyl-containing precursor transformed into a labelling reagent, such as described above, by transforming the carbonyl function into a diazo function by a Bamford Stevens type reaction.

6. A process for labelling a biological molecule, comprising contacting the biological molecule with the labelling reagent according to claim 1 in a homogeneous solution, in an aqueous buffer that contains at least 50% water.

7. A labelled biological molecule obtained by the process according to claim 6, wherein the biological molecule is selected from the group consisting of nucleic acids, antigens, antibodies, polypeptides, and proteins.

8. A process for labelling and fragmenting a single or double strand nucleic acid comprising:
   fragmenting the nucleic acid,
   attaching a label onto at least one of the fragments with the labelling reagent according to claim 1,
   the reagent coupling covalently and mainly onto at least one phosphate of the said fragment.

9. The process according to claim 8, wherein the labelling is effected in an aqueous homogeneous solution that contains at least 50% water.

10. A labelled nucleic acid obtained by the process according to claim 8.

11. A kit for detection of a target nucleic acid containing the labelled nucleic acid according to claim 10.

12. A solid support onto which is attached the labelling reagent according to claim 1.

13. A process for capturing nucleic acids comprising:
   attaching directly or indirectly to a solid support at least one biological molecule according to claim 7,
   contacting the solid support with a biological sample capable of containing free nucleic acids, and then washing the solid support.

14. A labelling reagent of formula (D):

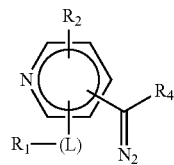

in which:
   $R_1$ represents a detectable label or at least two detectable labels linked together by at least one multimeric structure,
   $R_2$ represents: H, $NO_2$, Cl, Br, F, I, OR, SR, $NR^2$, R, NHCOR, CONHR, or COOR, where R=an alkyl or an aryl group,
   $R_4$ represents: H, an alkyl group, or an aryl group, and
   L is a linking arm comprising a $[-(O-CH_2-CH_2)-]_p$ moiety, where p is an integer from 1 to 20.

15. A process for synthesizing the labelling reagent according to claim 14, comprising:
   a) esterifying an aromatic dicarboxylic acid to form a diester,
   b) regioselectively substituting the diester with a compound derived from a mono-protected aminated ethylene glycol to form a precursor protected on a carboxyl function and an amine function,
   c) reducing the precursor to an alcohol and then oxidizing the alcohol to an aldehyde,
   d) acid treating the aldehyde to concomitantly protect the aldehyde function while deprotecting the amine function, to form an aminated acetal,
   e) reacting the aminated acetal with a detectable label the carboxyl function whereof is activated to form a precursor containing a detectable label,
   f) deprotecting the carbonyl function of the labelled precursor to form a labelled and carbonyl-containing precursor, and then
   g) transforming the labelled and carbonyl-containing precursor transformed into a labelling reagent, such as described above, by transforming the carbonyl function into a diazo function by a Bamford Stevens type reaction.

16. A process for labelling a biological molecule, comprising contacting the biological molecule with the labelling reagent according to claim 14 in a homogeneous solution, in an aqueous buffer that contains at least 50% water.

17. A labelled biological molecule obtained by the process according to claim 16.

18. A process for labelling and fragmenting a single or double strand nucleic acid comprising:
   fragmenting the nucleic acid,
   attaching a label onto at least one of the fragments with the labelling reagent according to claim 14,
   the reagent coupling covalently and mainly onto at least one phosphate of the said fragment.

19. The process according to claim 18, wherein the labelling is effected in an aqueous homogeneous solution that contains at east 50% water.

20. A labelled nucleic acid obtained by the process according to claim 18.

21. A kit for detection of a target nucleic acid containing the labelled nucleic acid according to claim 20.

22. A solid support onto which is attached the labelling reagent according to claim 14.

23. A process for capturing nucleic acids, comprising:
attaching directly or indirectly to a solid support at least one biological molecule according to claim 17,
contacting the solid support with a biological sample capable of containing free nucleic acids, and then
washing the solid support.

* * * * *